(12) United States Patent
Abdelrahman et al.

(10) Patent No.: US 10,919,030 B2
(45) Date of Patent: Feb. 16, 2021

(54) FORMING DIENES FROM CYCLIC ETHERS AND DIOLS, INCLUDING TETRAHYDROFURAN AND 2-METHYL-1,4-BUTANEDIOL

(71) Applicant: Regents of the University of Minnesota, Minneapolis, MN (US)

(72) Inventors: Omar A. Abdelrahman, Minneapolis, MN (US); Charles S. Spanjers, Minneapolis, MN (US); Dae Sung Park, Minneapolis, MN (US); Michael Tsapatsis, Edina, MN (US); Limin Ren, Minneapolis, MN (US); Paul J. Dauenhauer, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/337,600

(22) PCT Filed: Sep. 29, 2017

(86) PCT No.: PCT/US2017/054550
§ 371 (c)(1),
(2) Date: Mar. 28, 2019

(87) PCT Pub. No.: WO2018/064599
PCT Pub. Date: Apr. 5, 2018

(65) Prior Publication Data
US 2019/0345078 A1    Nov. 14, 2019

Related U.S. Application Data

(60) Provisional application No. 62/419,202, filed on Nov. 8, 2016, provisional application No. 62/419,247, filed
(Continued)

(51) Int. Cl.
*C07C 1/24* (2006.01)
*B01J 29/85* (2006.01)
(Continued)

(52) U.S. Cl.
CPC ............... *B01J 29/85* (2013.01); *B01J 29/40* (2013.01); *B01J 29/7007* (2013.01); *B01J 37/28* (2013.01);
(Continued)

(58) Field of Classification Search
CPC ........... C07C 1/24; C07C 15/08; C07C 2/865; C07C 6/06; C07C 11/04; C07C 11/06;
(Continued)

(56) References Cited

U.S. PATENT DOCUMENTS

| 1,094,223 A | 4/1914 | Kyriakides |
| 2,174,280 A | 9/1939 | Wellman |

(Continued)

FOREIGN PATENT DOCUMENTS

| EP | 0307060 | 3/1989 |
| RU | 2153924 | 8/2000 |

(Continued)

OTHER PUBLICATIONS

Abdelrahman et al., "Biomass-Derived Butadiene by Dehydra-Decyclization of Tetrahydrofuran" ACS Sustain. Chem. Eng., 5:3732-6, Apr. 2017.
(Continued)

*Primary Examiner* — Sharon Pregler
(74) *Attorney, Agent, or Firm* — Fish & Richardson P.C.

(57) ABSTRACT

Forming a diene includes contacting a reactant including at least one of a cyclic ether and a diol with a heterogeneous acid catalyst to yield a reaction mixture including a diene. The heterogeneous acid catalyst includes at least one of a Lewis acid catalyst, a supported Lewis-acid catalyst, a
(Continued)

Brønsted acid catalyst, a solid acid catalyst, a supported phosphoric acid catalyst, and a sulfonated catalyst. The dehydration of cyclic ethers and diols with high selectivity to yield dienes completes pathways for the production of dienes, such as isoprene and butadiene, from biomass in high yields, thereby promoting economical production of dienes from renewable resources.

42 Claims, 5 Drawing Sheets

Related U.S. Application Data on Nov. 8, 2016, provisional application No. 62/410,919, filed on Oct. 21, 2016, provisional application No. 62/402,238, filed on Sep. 30, 2016, provisional application No. 62/414,302, filed on Oct. 28, 2016, provisional application No. 62/410,922, filed on Oct. 21, 2016.

(51) Int. Cl.

| | | |
|---|---|---|
| B01J 29/40 | (2006.01) | |
| B01J 29/70 | (2006.01) | |
| B01J 37/28 | (2006.01) | |
| C07C 2/86 | (2006.01) | |
| C07C 6/06 | (2006.01) | |
| C07C 51/42 | (2006.01) | |

(52) U.S. Cl.
CPC ............... *C07C 1/24* (2013.01); *C07C 2/865* (2013.01); *C07C 6/06* (2013.01); *C07C 51/42* (2013.01); *B01J 2229/37* (2013.01); *C07C 2521/04* (2013.01); *C07C 2521/06* (2013.01); *C07C 2521/08* (2013.01); *C07C 2521/10* (2013.01); *C07C 2521/12* (2013.01); *C07C 2521/18* (2013.01); *C07C 2523/10* (2013.01); *C07C 2523/20* (2013.01); *C07C 2527/167* (2013.01); *C07C 2527/18* (2013.01); *C07C 2527/188* (2013.01); *C07C 2529/08* (2013.01); *C07C 2529/40* (2013.01); *C07C 2529/70* (2013.01)

(58) Field of Classification Search
CPC ............... C07C 2521/04; B01J 2229/16; B01J 2229/37; B01J 29/40; B01J 29/7007; B01J 29/82; B01J 29/85; B01J 37/28; Y02P 20/52; Y02P 20/582
See application file for complete search history.

(56) References Cited

U.S. PATENT DOCUMENTS

| | | | |
|---|---|---|---|
| 2,310,809 A | 2/1943 | Reppe et al. | |
| 3,758,612 A | 9/1973 | Maurin | |
| 3,781,222 A | 12/1973 | Weisang et al. | |
| 3,849,512 A * | 11/1974 | Bowman .................. | B01J 27/18 |
| | | | 585/611 |
| 3,893,946 A | 7/1975 | Weisang et al. | |
| 3,957,900 A | 5/1976 | Weisang et al. | |
| 3,987,900 A | 10/1976 | Tadokoro et al. | |
| 5,849,970 A | 12/1998 | Fall et al. | |
| 6,248,924 B1 | 6/2001 | Rühl et al. | |
| 8,067,214 B2 | 11/2011 | Burk et al. | |
| 8,580,543 B2 | 11/2013 | Burk et al. | |
| 8,981,172 B2 | 3/2015 | Norman | |
| 9,169,496 B2 | 10/2015 | Marliere | |
| 9,180,413 B2 | 11/2015 | Tsapatsis et al. | |
| 2003/0004383 A1 | 1/2003 | Brown et al. | |
| 2010/0216958 A1 | 8/2010 | Peters et al. | |
| 2013/0059722 A1 | 3/2013 | Tsapatsis et al. | |
| 2014/0296600 A1 | 10/2014 | Dauenhauer et al. | |
| 2019/0241481 A1* | 8/2019 | Delledonne .............. | B01J 23/10 |
| 2019/0344252 A1 | 11/2019 | Cho et al. | |

FOREIGN PATENT DOCUMENTS

| | | |
|---|---|---|
| RU | 2183499 | 6/2002 |
| WO | WO 2001/37994 | 5/2001 |
| WO | WO 2016/092063 | 6/2016 |

OTHER PUBLICATIONS

Camblor et al., "Spontaneous nucleation and growth of pure silica zeolite-beta free of connectivity defects," Chem. Comm., 2365-6, Jul. 1996.
Chang et al., "Lewis acid zeolites for tandem Diels-Alder cycloaddition and dehydration of biomass-derived dimethylfuran and ethylene to renewable p-xylenem," Green Chem, 18:1368-76, 2016.
Chang et al., "Rapid synthesis of Sn-Beta for the isomerization of cellulosic sugars," RSC Adv., 2(28):10475-7, Sep. 2012.
Chang et al., "Ultra-selective cycloaddition of dimethylfuran for renewable p-xylene with H-BEA," Green Chem., 16:585-88, 2014.
Chia et al., "Selective Hydrogenolysis of Polyols and Cyclic Ethers over Bifunctional Surface Sites on Rhodium-Rhenium Catalysts" J. Am. Chem. Soc., 133:12675-89, Jul. 2011.
Cho et al., "Renewable p-Xylene from 2,5-Dinethylfuran and Ethylene Using Phosphorus-Containing Zeolite Catalysts," ChemCatChem., 9(3):398-402, Feb. 2017.
Choi et al., "Amphiphilic organosilane-directed synthesis of crystalline zeolite with tunable mesoporosity," Nat. Mater., 5: 718-23, Sep. 2006.
Choi et al., "Stable single-unit-cell nanosheets of active and long-lived catalysts," Nature, 461:246-9, Sep. 2009.
Choudhary et al.,"Conversion of Xylose to Furfural Using Lewis and Brønsted Acid Catalysts in Aqueous Media," ACS Catalysis 2(9):2022-8, Aug. 2012.
Duan et al., "Efficient production of 1,3-butadiene in the catalytic dehydration of 2,3-butanediol," Applied Catalysis A: General 491:163-9, Feb. 2015.
Farneth and Gorte, "Methods for Characterizing Zeolite Acidity," Chem. Rev., 95(3):615-35, May 1995.
Freidlin and Sharf, "Two paths for the dehydration of 1,4-butandiol to divinyl with a tricalcium phosphate catalyst," Bull. Acad. Sci. USSR, Div. Chem. Sci. 9(9):1577-9, Feb. 1960.
Fyfe et al., "Detailed Investigation of the Lattice Structure of Zeolite ZSM-11 by a Combination of Solid-State NMR and Synchrotron X-ray Diffraction Techniques," J. Am. Chem. Soc., 111(7):2470-4, Mar. 1989.
Godawa et al., "Palladium catalyzed hydrogenation of furan: optimization of production conditions for tetrahydrofuran," Resources, Conservation and Recycling 3(4):201-16, Jun. 1990.
Gorte, "What do we know about the acidity of solid acids?," Catalysis Letters, 62(1):1-13, Sep. 1999.
Groen et al., "Desilication: on the controlled generation of mesoporosity in MFI zeolites," Mater. Chem., 16:2121-31, Mar. 2006.
Ichikawa et al., "Catalytic reaction of 1,3-butanediol over solid acids," J. Mol. Catal. A: Chem. 256(1-2):106-12, Aug. 2006.
Igarashi et al., "Dehydration of butanediols over CeO2 catalysts with different particle sizes," Applied Catalysis A: General 300(1):50-7, Jan. 2006.
Jeong et al., "Oriented Molecular Sieve Membranes by Heteroepitaxial Growth," J. Am. Chem. Soc., 124(44):12966-8, Nov. 2002.
Jiang et al. "Biodegradation-inspired bioproduction of methylacetoin and 2-methyl-2, 3-butanediol" Sci. Rep., 3:1-7, Aug. 2013.
Jing et al., "Direct Dehydration of 1,3-butaneidol into butadiene over aluminosilicate catalysts," Catal. Sci. Technol., 6(15):5830-40, Feb. 2016.
Kragten et al., "Structure of the Silica Phase Extracted from Silica/(TPA)OH Solutions Containing Nanoparticles," J. Phys. Chem. B, 107(37):10006-16, Sep. 2003.

(56) References Cited

OTHER PUBLICATIONS

Lee et al., "Sub-40 nm Zeolite Suspensions via Disassembly of Three-Dimensionally Ordered Mesoporous-Imprinted Silicalite-1," J. Am. Chem. Soc., 133(3):493-502, Jan. 2011.
Lejemble et al., "From biomass to furan through decarbonylation of furfural under mild conditions," Biomass, 4(4):263-74, Jan. 1984.
Li et al., "Pure-Silica-Zeolite MEL Low-k Films from Nanoparticle Suspensions," J. Phys. Chem. B., 109(18):8652-8, May 2005.
Liu et al., Catalytic Behavior of Bronsted Acid Sites in MWW and MFI Zeolites with Dual Meso- and Microporosity ACS Catal., 1(1):7-17, Jan. 2011.
Maheshwari et al., "Layer Structure Preservation during Swelling, Pillaring, and Exfoliation of a Zeolite Precursor," J. Am. Chem. Soc., 130(4):1507-16, Jan. 2008.
Makshina et al., "Review of old chemistry and new catalytic advances in the on-purpose synthesis of butadiene," Chem. Soc. Rev., 43(22), 7917-53, Mar. 2014.
Na et al., "Pillared MFI Zeolite Nanosheets of a single-Unit-Cell Thickness," J. Am. Chem. Soc., 132(12):4169-77, Mar. 2010.
Nair et al., "Zeolite-β grown epitaxially on SSZ-31 nanofibers," Chem. Commun., 10:921-2, Mar. 1999.
Pace et al., "2-Methyltetrahydrofuran (2-MeTHF): A Biomass-Derived Solvent with Broad Application in Organic Chemistry," ChemSusChem., 5(8):1369-79, Aug. 2012.
PCT International Preliminary Report on Patentability in International Appln. No. PCT/US2017054550 dated Apr. 11, 2019, 7 pages.
PCT International Search Report and Written Opinion in International Appln. No. PCT/US2017054550 dated Dec. 12, 2017, 13 pages.
Roth et al., "MCM-36: The first pillared molecular sieve with zeolite properties," Stud. Surf. Sci. and Catal., 94:301, Jan. 1995.
Sato et al., "Dehydration of 1,4-butanediol into 3-buten-1-ol catalyzed by ceria," Catal. Comm., 5(8):397-400, Aug. 2004.
Sato et al., "Dehydration of diols catalyzed by CeO2," J. Mol. Catal. A: Chem., 221(1-2):177-83, Nov. 2004.
Sayari et al., "Simple Synthesis Route to Monodispersed SBA-15 Silica Rods," J. Am. Chem. Soc., 126(44)14348-9, Oct. 2004.
Schlenker et al., "Computed X-ray Powder Diffraction Patterns for Ultrasmall Zeolite Crystals," J. Appl. Cryst., 29(2):178-85, Apr. 1996.
Sharf et al., "Production of isoprene from formaldehyde and isobutylene through 3-methylbutanediol-1, 3," Bull. Acad. Sci. USSR, Div. Chem. Sci., 14(9), 1621-3, Sep. 1965.
Shuikin and An, "Dehydration of tetrahydropyran over TiO2—Al2O3," Bull. Acad. Sci. USSR, Div. Chem. Sci., 9(8):1400-140, Jan. 1960.
Smith and Fuzek, "Catalytic Hydrogenation of Furan and Substituted Furans on Platinum," J. Am. Chem. Soc., 71(2):415-9, Feb. 1949.
Spanjers et al., "Branched Diol Monomers from the Sequential Hydrogenation of Renewable Carboxylic Acids," ChemCatChem., 8(19):3031-5, Oct. 2016.
Tsapatsis et al., "A New, Yet Familiar, Lamellar Zeolite," ChemCatChem., 2:246-8, Mar. 2010.
Tsapatsis et al., "Pores by Pillaring: Not Always a Maze," Angew. Chem. Int. Ed., 47(23):4262-3, May 2008.
Van Koningsveld et al., "The monoclinic framework structure of zeolite H-ZSM-5. Comparison with the orthorhombic framework of as-synthesized ZSM-5", Zeolites, 10:235-42, May 1990.
Yang and Seng, "One-Step Catalytic Transformation of Carbohydrates and Cellulosic Biomass to 2,5-Dimethyltetrahydrofuran for Liquid Fuels," ChemSusChem., 3(5):597-603, May 2010.
Yim et al., "Metabolic engineering of *Escherichia coli* for direct production of 1,4-butanediol," Nat. Chem. Biol., 7(7):445-52, May 2011.
Yokoi et al.,"Periodic Arrangement of Silica Nanospheres Assisted by Amino Acids," J. Am. Chem. Soc., 128(42) 13664-5, Oct. 2006.
Zhang et al., "Synthesis of Self-Pillared Zeolite Nanosheets by Repetitive Branching," Science 336(6089):1684-7, Jun. 2012.
U.S. Appl. No. 16/337,603, filed Mar. 28, 2019, Hong Je Cho, Published.

* cited by examiner

FORMING DIENES FROM CYCLIC ETHERS AND DIOLS, INCLUDING TETRAHYDROFURAN AND 2-METHYL-1,4-BUTANEDIOL

CROSS-REFERENCE TO RELATED APPLICATIONS

This application is a National Stage application under 35 U.S.C. § 371 of International Application No. PCT/US2017/054550, having an International Filing Date of Sep. 29, 2017, which claims the benefit of U.S. Application Ser. No. 62/402,238 entitled "USE OF PHOSPHORUS-CONTAINING SOLID CATALYSTS" filed Sep. 30, 2016; U.S. Application Ser. No. 62/410,919 entitled "METHODS OF FORMING ISOPRENE FROM 2-METHYL-1,4-BUTANEDIOL, DERIVATIVES OR COMBINATIONS THEREOF" filed Oct. 21, 2016; U.S. Application Ser. No. 62/410,922 entitled "METHODS OF FORMING DIENES FROM TETRAHYDROFURAN, DERIVATIVES OR COMBINATIONS THEREOF" filed Oct. 21, 2016; U.S. Application Ser. No. 62/414,302 entitled "PHOSPHORUS-CONTAINING SOLID CATALYSTS AND METHODS OF USE THEREOF" filed Oct. 28, 2016; U.S. Application Ser. No. 62/419,202 entitled "METHODS OF FORMING ISOPRENE FROM 2-METHYL-1,4-BUTANEDIOL, DERIVATIVES OR COMBINATIONS THEREOF" filed Nov. 8, 2016; and U.S. Application Ser. No. 62/419,247 entitled "METHODS OF FORMING DIENES FROM TETRAHYDROFURAN, DERIVATIVES, OR COMBINATIONS THEREOF" filed Nov. 8, 2016, all of which are incorporated by reference herein in their entirety.

STATEMENT OF GOVERNMENT INTEREST

This invention was made with government support under CHE-1413862 awarded by the National Science Foundation. The government has certain rights in the invention.

BACKGROUND

Some dienes, such as butadiene and isoprene, are used to produce rubbery polymers (e.g., for use in car tires). These dienes are commonly produced from the cracking of naptha and other petroleum-derived precursors. Although these dienes can be produced from renewable resources such as bio-based feedstocks, yields are generally low, making these processes cost prohibitive. In one example, depicted in Scheme 1, furfural can be formed from xylose, a readily available biomass-derived platform molecule. Furfural can then be converted to furan through decarbonylation, followed by hydrogenation to yield tetrahydrofuran. Dehydra-decyclization of tetrahydrofuran yields butadiene, completing the pathway for the production of butadiene from biomass.

Scheme 1

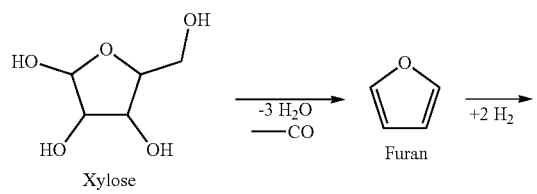

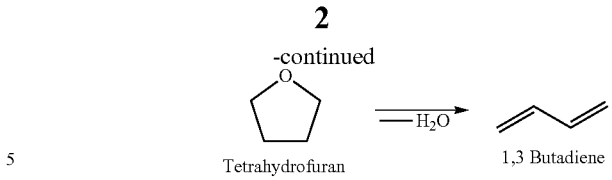

Synthetic methods with improved diene yields would make production of dienes from renewable resources economically feasible.

SUMMARY

In a general aspect, forming a diene includes contacting a reactant with a heterogeneous acid catalyst to yield a reaction mixture including a diene, where the reactant includes a cyclic ether or a diol. The heterogeneous acid catalyst includes at least one of a Lewis acid catalyst, a solid Lewis-acid catalyst, a Brønsted acid catalyst, a solid acid catalyst, a supported phosphoric acid catalyst, and a sulfonated catalyst.

Implementations of the general aspect may include one or more of the following features.

The reactant may be derived from biomass. When the reactant is a cyclic ether, the cyclic ether may have tetrahydrofuran skeleton. In some embodiments, the cyclic either is tetrahydrofuran, and the diene is butadiene. A selectivity of the butadiene is typically at least 95%. In some embodiments, the cyclic ether is 2-methyltetrahydrofuran, and the diene is pentadiene. A selectivity of the pentadiene is typically at least 95%. In some embodiments, the cyclic ether is 2,5-dimethyl tetrahydrofuran and the diene is hexadiene. A selectivity of the hexadiene is typically at least 90%. In some embodiments, the cyclic ether is 3-methyltetrahydrofuran, and the diene is isoprene. A selectivity of the isoprene is typically at least 65%. When the cyclic ether is 3-methyltetrahydrofuran, forming the diene may include processing biomass to yield citric acid, itaconic acid, or mesaconic acid, and processing the citric acid, itaconic acid, or mesaconic acid to yield the 3-methyltetrahydrofuran. That is, the 3-methyltetrahydrofuran may be formed from at least one of citric acid, itaconic acid, and mesaconic acid derived from biomass. When the reactant is a diol, the diol may be 2-methyl-1,4-butanediol, and the diene is isoprene. A selectivity of the isoprene is typically at least 70%.

In some implementations, the contacting occurs at a temperature from 100° C. to 600° C., 150° C. to 400° C., 100° C. to 500° C., or 200° C. to 300° C. The contacting may occur at a pressure from 0 psia to 500 psia (34 atm), at a pressure up to 147 psia (10 atm), at pressure from 1 atm to 10 atm, or from 1 atm to 2 atm. In some cases, the contacting occurs in the presence of an inert gas, such as He, Ar, and $N_2$. In certain cases, the contacting occurs in the vapor phase. Some implementations may include separating the diene from the reaction mixture. The reaction mixture may include unreacted cyclic ether, unreacted diol, or both, and the unreacted cyclic ether, unreacted diol, or both may be contacted with the heterogeneous acid catalyst to yield the diene.

In some implementations, the heterogeneous acid catalyst includes a Lewis acid catalyst, and the Lewis acid catalyst includes at least one of $AlCl_3$, $TiCl_4$, $FeCl_3$, $BF_3$, $SnCl_4$, $ZnCl_2$, $ZnBr_2$, AMBERLYST-70, $SiO_2$, $Nb_2O_5$, MgO, $TiO_2$, $SiO_2$—$Al_2O_3$, $CeO_2$, and $Cr_2O_3$.

In some implementations, the heterogeneous acid catalyst includes a Brønsted acid catalyst, and the Brønsted acid catalyst includes at least one of HCl, HBr, HI, HClO$_4$, HClO$_3$, HNO$_3$, H$_2$SO$_4$, CH$_3$COOH, CF$_3$COOH, and H$_3$PO$_4$.

In some implementations, the heterogeneous acid catalyst includes a solid acid catalyst, and the solid acid catalyst includes at least one of a zeolite type catalyst, a substituted-zeolite type catalyst, a heteropolyacid type catalyst, a phosphate type catalyst, a zirconia type catalyst, a celite type catalyst, a metal organic framework type catalyst, a carbon type catalyst, and a sulfonic acid catalyst. Suitable zeolite type catalysts include H-ZSM-5, H-BEA, H-Y, mordenite, ferrierite, chabazite, and self-pillared pentasil. The self-pillared pentasil typically has an average pore size of at least 5 Å. Suitable phosphorus-containing zeolite type catalysts include phosphorus-containing MFI, phosphorus-containing MEL, phosphorus-containing BEA, phosphorus-containing FAU, phosphorus-containing MOR, phosphorus-containing FER, phosphorus-containing CHA, and phosphorus-containing self-pillared pentasil. The phosphorus-containing self-pillared pentasil has a ratio of silicon atoms to phosphorus atoms in a range of 1:1 to 1000:1 or 3:1 to 150:1. The phosphorus-containing self-pillared pentasil has rotational intergrowths of single-unit-cell lamellae that lead to repetitive branching nanosheets. The nanosheets have a thickness of about 2 nm and define a network of micropores having a diameter of about 0.5 nm. The phosphorus-containing self-pillared pentasil has a house of cards arrangement defining a network of mesopores having a dimension in a range of 2 nm to 7 nm. The phosphorus-containing zeolite type catalyst is substantially free of aluminum. That is, the phosphorus-containing zeolite type catalyst may include less than 5 wt %, less than 4 wt %, less than 3 wt %, less than 2 wt %, or less than 1 wt % of aluminum. Suitable substituted zeolite type catalyst include Sn, Ge, Ga, B, Ti, Fe, and Zr.

Suitable heteropolyacid type catalysts include H$_3$PW$_{12}$O$_{40}$, H$_3$SiW$_{12}$O$_{40}$, H$_5$AlW$_{12}$O$_{40}$, H$_6$CoW$_{12}$O$_{40}$, H$_3$PMo$_{12}$O$_{40}$, H$_3$SiMo$_{12}$O$_{40}$, and Cs$^+$ substituted heteropolyacid type catalyst.

Suitable phosphate type catalysts include niobium phosphate (NbOPO$_4$), zirconium phosphate (ZrO$_2$—PO$_4$), siliconiobium phosphate (Nb—P—Si—O), tricalcium phosphate (Ca$_3$(PO$_4$)$_2$), lithium phosphate (Li$_3$PO$_4$), and lithium sodium phosphate (Li$_3$NaP$_2$O$_7$).

Suitable zirconia type catalysts include SO$_3$—ZrO$_2$, SiO$_2$—ZrO$_2$, Zeolites-ZrO$_2$, Al$_2$O$_3$—ZrO$_2$, ZrO$_2$, and WO$_x$—ZrO$_2$.

Suitable celite type catalysts include P-CELITE.

Suitable metal organic framework catalysts include MTh 101.

Suitable carbon type catalysts include activated carbon, sulfated carbon, and SO$_3$H-functionalized carbon.

Suitable sulfonated catalysts include NAFION and AMBERLYST.

Advantages of processes described herein include dehydration of cyclic ethers and diols with high selectivity to yield dienes, there by completing pathways for the production of dienes, such as isoprene and butadiene, from biomass in high yields. These synthetic methods facilitate economical production of dienes from renewable resources.

DETAILED DESCRIPTION

Disclosed herein are processes and methods for the dehydration of cyclic ethers and diols over heterogeneous acid catalysts to produce dienes. Examples of suitable cyclic ethers include furans (compounds with a tetrahydrofuran skeleton), including tetrahydrofuran (THF), 2-methyltetrahydrofuran (2-MTHF), 3-methyltetrahydrofuran (3-MTHF), and 2,5 dimethyltetrahydrofuran (2,5-DMTHF). Examples of suitable diols include butanediols, such as 2-methyl-1,4-butanediol (MBDO). The particular diene produced depends on the reactant (e.g., the cyclic ether or diol) and the reaction conditions (e.g., temperature or pressure). In some embodiments, dienes produced include 1,3-butadiene ("butadiene"), 2-methyl-1,3-butadiene (isoprene), pentadiene, and hexadiene.

One embodiment, depicted in Scheme 2, includes a process for the dehydra-decyclization of tetrahydrofuran (THF) over a heterogeneous acid catalyst to yield 1,3-butadiene and water. The THF may be obtained from any biomass-derived source, such as biomass-derived furan. This process, which completes the pathway for the production of butadiene from biomass depicted in Scheme 1, results in a high yield of 1,3-butadiene, with a selectivity of at least 95%.

Scheme 2

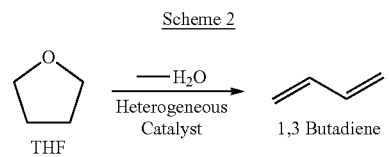

Another embodiment, depicted in Scheme 3, includes a process for the dehydration of 2-methyltetrahydrofuran (2-MTHF), which can be readily derived from biomass, over a heterogeneous acid catalyst to yield pentadiene with a selectivity of at least 95%.

Scheme 3

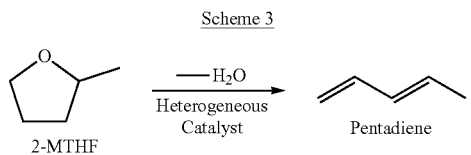

Yet another embodiment, depicted in Scheme 4, includes a process for the dehydration of 2,5 dimethyltetrahydrofuran (2,5-DMTHF), which can be readily derived from biomass, over a heterogeneous acid catalyst to yield hexadiene with a selectivity of at least 90%.

Scheme 4

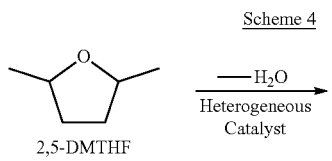

Scheme 6

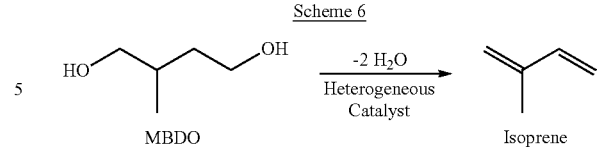

Another embodiment, depicted in Scheme 5, includes a process for the dehydration of 3-methyltetrahydrofuran (3-MTHF), which can be readily derived from biomass, over a heterogeneous acid catalyst to yield isoprene. The selectivity to isoprene of this reaction is at least 65%.

Scheme 5

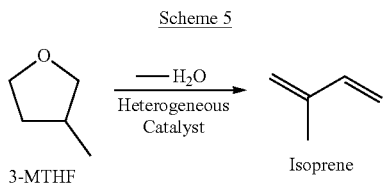

Still another embodiment, depicted in Scheme 6, includes a process for dehydration of 2-methyl-1,4-butanediol (MBDO), which can be readily derived from biomass, over a heterogeneous acid catalyst to yield isoprene with a selectivity of at least 70%. In some examples, MBDO is produced from biomass-derived citric acid, itaconic acid, or mesaconic acid. Thus, disclosed methods complete the pathway for the production of isoprene in high yields from biomass.

Figure 1:
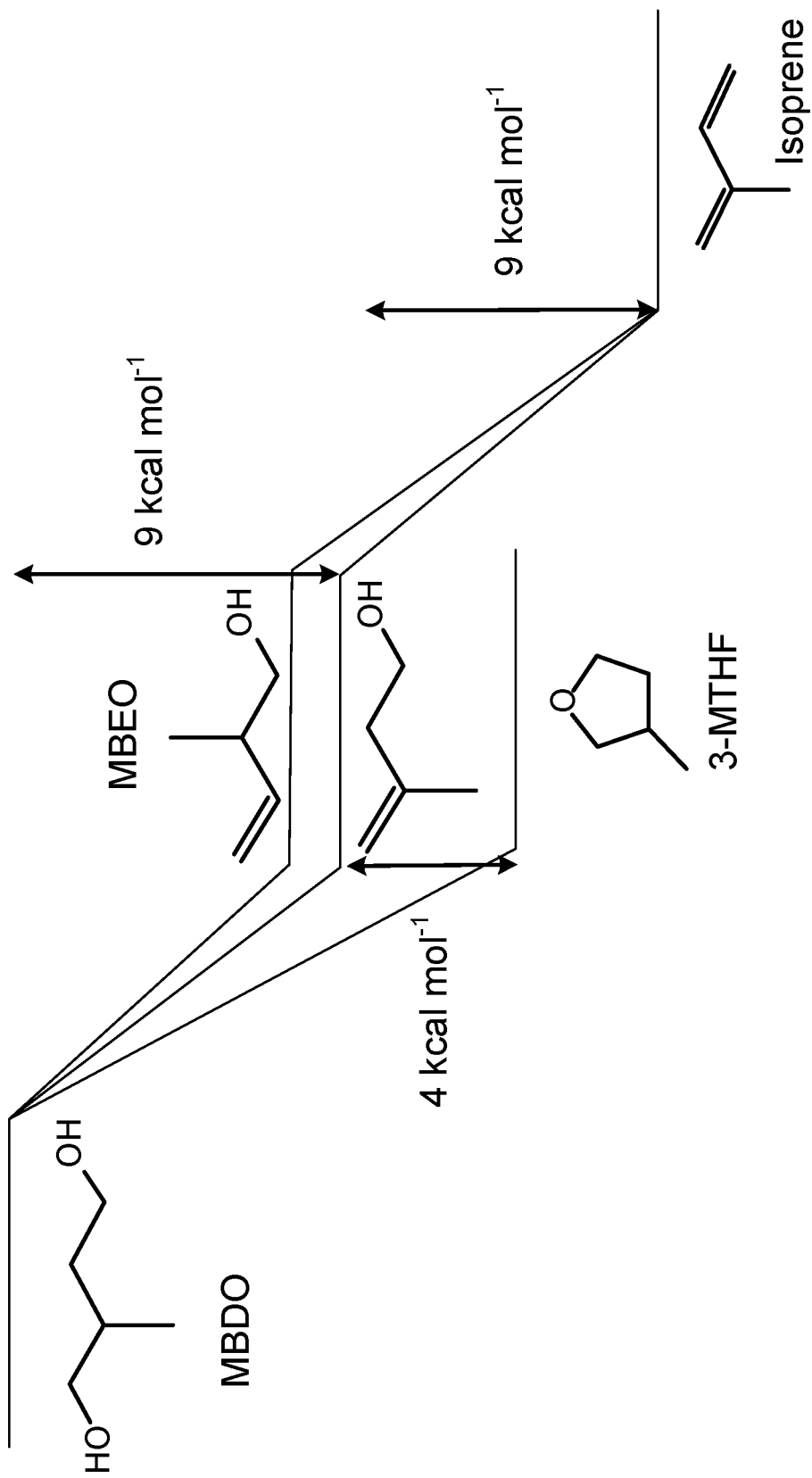
FIG. 1 depicts a reaction diagram for the dehydration of 2-methyl-1,4-butanediol (MBDO) to isoprene at 200° C. and 1 atm. Intermediates in the dehydration reaction include 3-methyltetrahydrofuran (3-MTHF), 2-methyl-3-butene-1-ol, and 3-methyl-3-butene-1-ol (MBEO).

FIG. 1 shows a calculated reaction energy diagram for MBDO dehydration. Isoprene is the thermodynamically preferred product at 200° C. and 1 atm pressure. At temperatures lower than 150° C., 3-MTHF becomes the preferred product. As such, greater selectivity for isoprene can be achieved at temperatures of at least about 150° C. The upper temperature limit (e.g., 400° C. or 600° C.) for producing isoprene is governed by bond-forming reactions of isoprene (e.g., Diels-Alder of two isoprene molecules to form limonene), coking reactions, and bond-breaking reactions, all of which may be favored at higher temperatures.

Dehydration reactions disclosed herein can be carried out with a variety of catalysts at a variety of temperatures, pressures, and space velocities (reactant volumetric flow rate per volume of catalyst). Suitable catalysts include acid catalysts, such as those listed in Table 1. In some embodiments, dehydration reactions described herein take place at an elevated temperature (relative to room temperature) over a heterogeneous acid catalyst. In certain embodiments, dienes can be produced from cyclic ethers or diols without adding water to the reaction, simplifying and reducing the cost of the process.

TABLE 1

Acid catalyst classes, types, and examples suitable for dehydration of cyclic ethers and diols to yield dienes.

| Class | Type | Example |
| --- | --- | --- |
| Lewis Acid (L-Acid) Catalysts | L-Acids | $AlCl_3$, $TiCl_4$, $FeCl_3$, $BF_3$, $SnCl_4$, $ZnCl_2$, $ZnBr_2$, Amberlyst-70 |
| | Solid L-Acids | $SiO_2$, $Al_2O_3$, $Nb_2O_5$, MgO $TiO_2$, $SiO_2$—$Al_2O_3$, $CeO_2$, $Cr_2O_3$ |
| Brønsted Acid (B-Acid) Catalysts | B-Acids | HCl, HBr, HI, $HClO_4$, $HClO_3$, $HNO_3$, $H_2SO_4$, $CH_3COOH$, $CF_3COOH$, $H_3PO_4$ |
| Solid Acid Catalysts | Zeolites (Z) | H-ZSM-5, H-BEA, H—Y, Mordenite, Ferrierite, Chabazite, Self-Pillared Pentasil (SPP), phosphorus-containing zeolites (e.g., P-BEA, P-MFI) |
| | Substituted Zeolites (Sub.) | Sn, Ge, Ti, Fe, Zr, P |
| | Heteropolyacids (HPAs) | $H_3PW_{12}O_{40}$, $H_5AlW_{12}O_{40}$, $H_6CoW_{12}O_{40}$, $H_3SiW_{12}O_{40}$, $H_3PMo_{12}O_{40}$, $H_3SiMo_{12}O_{40}$ ($Cs^+$ substituted HPAs) |
| | Phosphates ($PO_4^{3-}$) | Niobium phosphate ($NbOPO_4$), Zirconium phosphate ($ZrO_2$—$PO_4$), Siliconiobium phosphate (Nb—P—Si—O) Tricalcium phosphate ($Ca_3(PO_4)_2$) Lithium phosphate ($Li_3PO_4$) Lithium sodium phosphate ($Li_3NaP_2O_7$) |
| | Zirconias ($ZrO_2$) | $SO_3$—$ZrO_2$, $SiO_2$—$ZrO_2$, Zeolites-$ZrO_2$, $Al_2O_3$—$ZrO_2$, $ZrO_2$, $WO_x$—$ZrO2$ |
| | Celite ® | P-Celite ® |
| | Metal Organic Framework (MOF) | Metal organic framework |
| | Carbon (C) | Activated carbon, sulfated carbon ($SO_3H$-functionalized carbon) |

Other suitable catalysts include a supported phosphoric acid catalysts.

Other suitable catalysts include self-pillared pentasil (SPP). Phosphorus-containing-self-pillared pentasil (P-SPP) is a silica-based, self-pillared, hierarchical (containing both micropore and mesopore) zeolitic material. In some embodiments, the ratio of silicon to phosphorus in suitable P-SPP catalysts is typically in a range of 1 to 5. In certain embodiments, the ratio of silicon to phosphorus in suitable P-SPP catalysts is 50 or less, 500 or less, or 1000 or less. Examples of ranges for the ratio of silicon to phosphorus in suitable P-SPP catalysts include 1 to 1000, 5 to 500, and 5 to 50 (e.g., 27). P—SPP can be synthesized by a direct hydrothermal method using tetrabutylphosphonium hydroxide (TBPOH) as an organic structure directing agent, with TBPOH providing phosphorus for the P-SPP. The rotational intergrowths of single-unit-cell lamellae leads to repetitive branching nanosheets. The nanosheets can be about 2 nm thick and can contain a network of micropores having a diameter of about 0.5 nm. The house-of-cards arrangement of the nanosheets creates a network mesopores having a diameter in a range of about 2 nm to about 7 nm. As used herein, a micropore has a diameter of less than about 2 nm, and a mesopores has a diameter between about 2 nm and about 50 nm.

In some embodiments, other phosphorus-containing zeolites ("P-zeolites") can be utilized to form dienes from cyclic ethers and diols. Suitable P-zeolites include, for example P-BEA, P-MFI and P-MEL, P-FAU, P-MOR, P-FER, P-CHA, and P-SPP. One example, P-BEA can be prepared by impregnating a zeolite having a BEA framework with phosphoric acid, as described in Fan W. et al. (2016) Renewable p-Xylene from 2,5-Dimethylfuran and Ethylene Using Phosphorus-containing Zeolite Catalysts. *ChemCatChem* (2016) (DOI: 10.1002/cctc.201601294). In some cases, suitable P-zeolites are free or substantially free of aluminum. A P-zeolite that is "substantially free" of aluminum can include, for example, less than 5 wt %, less than 4 wt %, less than 3 wt %, less than 2 wt %, or less than 1 wt % of aluminum.

In some embodiments, P-Celite® prepared by impregnating Celite® with phosphoric acid can be used to form dienes from cyclic ethers and diols. P-Celite® may be made according to Fan W., et al. (2016) Renewable p-Xylene from 2,5-Dimethylfuran and Ethylene Using Phosphorus-containing Zeolite Catalysts. *ChemCatChem* (2016) (DOI: 10.1002/cctc.201601294).

In some embodiments sulfonated (e.g., sulfonic acid) catalysts can be utilized. Suitable sulfonic acid catalysts (also referred to as sulfonate catalysts) include NAFION and AMBERLYST.

The dehydration of cyclic ethers and diols to yield dienes can be carried out using any appropriate temperature. In some embodiments, the reaction can be carried out in the vapor phase. In some embodiments, the reaction can be carried out at temperatures of not less than 100° C., not less than 150° C., or not less than 200° C. In some embodiments the reaction can be carried out at a temperature of not greater than 600° C., not greater than 500° C., not greater than 400° C., not greater than 350° C., or not greater than 300° C. In some embodiments, the reaction can be carried out at a temperature from 100° C. to 600° C., from 150° C. to 400° C., from 100° C. to 500° C., or from 200° C. to 300° C. For selective formation of isoprene from 3-MTHF, suitable temperatures are from 150° C. to 350° C.

The dehydration of cyclic ethers or diols can be carried out at any appropriate pressure. In some embodiments the reaction pressure can be not less than vacuum (0 psia) or not less than 1 atm. In some embodiments, the reaction pressure can be 10 atm or less, or 2 atm or less. In some embodiments, the reaction pressure can be from vacuum (0 psia) to 500 psia, or from 1 atm to 2 atm. Low pressures may yield selective formation of certain dienes, such as isoprene, due to favorable thermodynamic conditions. Thus, in some cases, pressures less than 10 atm may be selected.

The dehydration of cyclic ethers or diols can be carried out at any appropriate space velocity. In some embodiments, space velocity can be chosen to obtain single-pass conversion of the cyclic either or diol that is less than 100%. In some embodiments, space velocity can be chosen such that 100% conversion is obtained. In certain embodiments, space velocity can be considerably higher than that necessary to obtain 100% conversion of the cyclic ether or diol.

Dehydration reactions described herein may be carried out with or without an inert carrier gas (e.g., He, Ar, $N_2$, etc.) added to or contacted with the cyclic ether or diol prior to the reactants entering a catalytic reactor with the catalyst.

Figure 2:
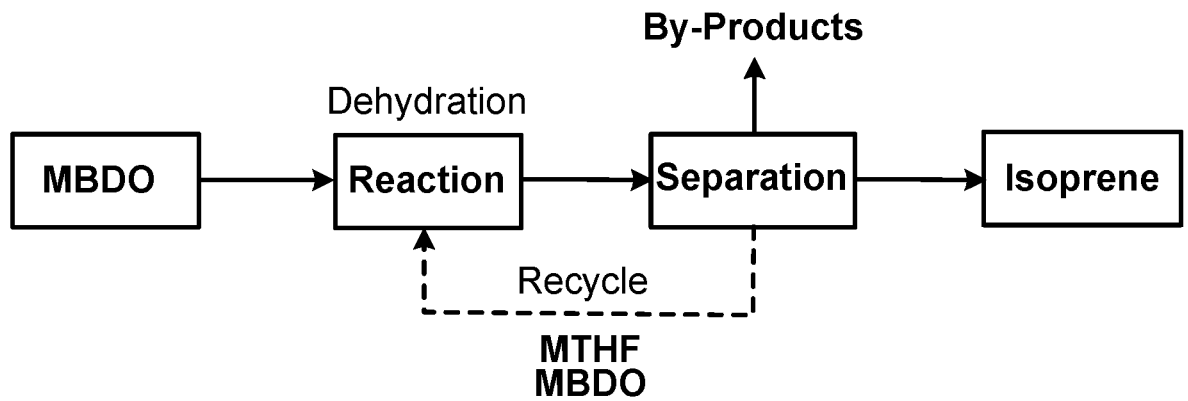
FIG. 2 shows a process scheme for the production of isoprene from MBDO with continuous recycling of 3-MTHF and MBDO.

Because the selectivity of the dehydration reactions disclosed herein to a particular diene may decrease with increasing conversion of the reactant (i.e., cyclic ether or diol), it may be useful to perform the process using a recycle stream of the reactant. In some embodiments, as depicted in FIG. 2, a reaction intermediate, such as 3-MTHF in the formation of isoprene from MBDO, may be recycled with the cyclic ether or diol.

In some embodiments, zeolites may be useful in the dehydration of cyclic ethers and diols to dienes (e.g., MBDO to isoprene). In particular, zeolites such as microporous aluminosilicates with pore sizes of not less than about 5 Å, not less than about 4 Å, or not less than about 3 Å may promote diene formation over that of other products (e.g., isoprene formation over 3-MTHF) based on the size of the reactant and product molecules.

This disclosure is further illustrated by the following examples. The particular examples, materials, amounts, and procedures are to be interpreted broadly in accordance with the scope and spirit of the disclosure as set forth herein.

Examples

Dehydra-Decyclization of Tetrahydrofurans

The following catalysts were tested for THF dehydra-decyclization: $CeO_2$ (Sigma Aldrich), H-ZSM-5 Zeolite (Zeolyst CBV28014 $SiO_2/Al_2O_3$ ratio=280), H-Y Zeolite (Zeolyst CBV760, $SiO_2/Al_2O_3$=60), H-BEA Zeolite (Zeolyst CBV811C-300 $SiO_2/Al_2O_3$ ratio=360), tin-BEA Zeolite (Sn-BEA) (Chang C-C, Wang Z, Dornath P, Je Cho H, & Fan W (2012) Rapid synthesis of Sn-Beta for the isomerization of cellulosic sugars. *RSC Advances* 2(28):10475-10477), $ZrO_2$ (Sigma Aldrich), phosphorous-self-pillared pentasil (P-SPP), phosphorous-celite (P-Celite) (Hong Je Cho, Limin Ren, Vivek Vattipalli, Yu-Hao Yeh, Nicholas Gould, Bingjun Xu, Raymond J. Gorte, Raul Lobo, Paul J. Dauenhauer, Michael Tsapatsis, and Wei Fan, Renewable p-Xylene from 2, 5-Dimethylfuran and Ethylene Using Phosphorus-Containing Zeolite Catalysts *ChemCatChem* 9 (3), 398-402, 2017) MgO (Alfa Aesar), tricalcium phosphate (TCP, Sigma Aldrich), $SiO_2$—$Al_2O_3$(Sigma Aldrich), activated carbon (Sigma Aldrich), metal organic framework catalyst (MOF) (e.g., MIL 101), niobium oxide ($Nb_2O_5$, Sigma Aldrich), phosphotungstic acid (PTA, $H_3PW_{12}O_{40}$). All catalysts were pressed, crushed, and sieved to a particle size of 0.5 to 1 mm. With the exception of MOF, all catalysts were pre-treated under flowing He at 400° C. for 1 h. MOF was pre-treated under flowing He at 150° C. for 1 h.

Figure 3:
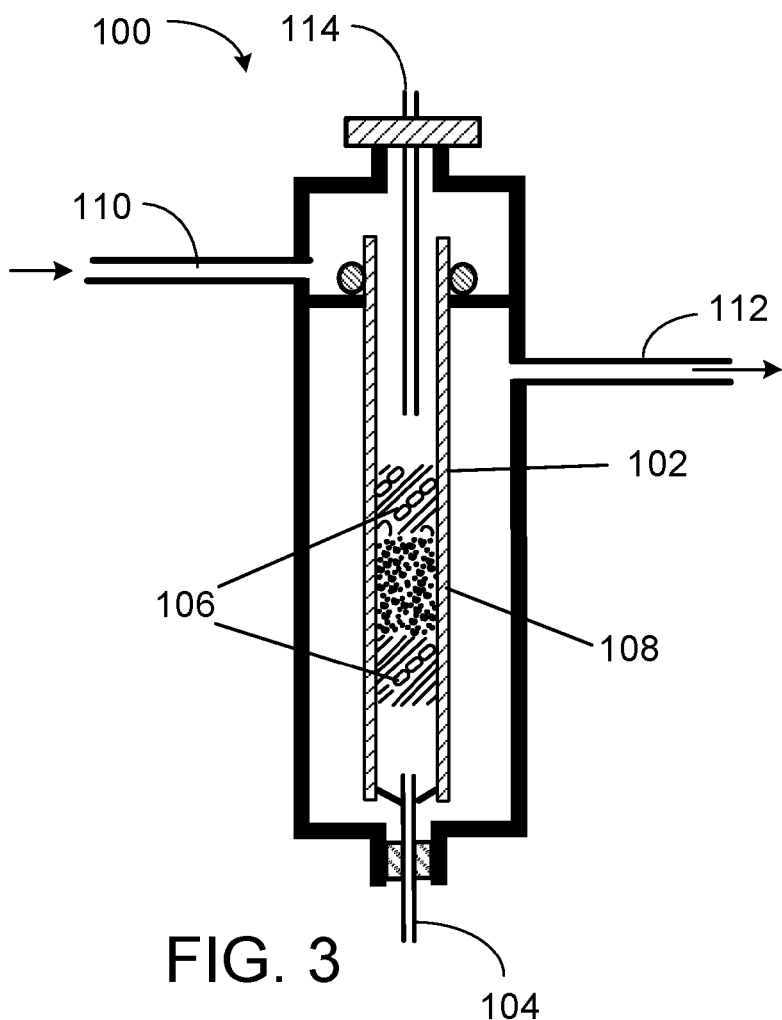
FIG. 3 depicts of high throughput pulsed flow reactor (HTPFR).

Dehydration reactions were performed in a high throughput pulsed flow reactor (HTPFR), such as HTPFR 100 depicted in FIG. 3. HTPFR 100 includes a glass reactor (i.e., inlet liner) 102 coupled to a gas chromatograph (Aglient 7890A) via conduit 104. Glass reactor 102 is packed with quartz wool 106 (7.5 mg and 15 mg) and catalyst 108 (5-200 mg). Carrier gas is provided to glass reactor 102 via inlet 110, and gas exits via split vent 112. Reactant is provided to HTPFR 100 through injection needle 114.

Experiments were performed at reaction temperatures of 200 to 400° C. The space velocity was controlled by adjusting the carrier gas (He, 99.999%) flow rate to the split vent. Space velocities of 10-89 $s^{-1}$ were tested with the reactor, where space velocity is defined as follows:

$$S = \text{space velocity} = \frac{F_{He}}{V_C} [=] \min^{-1}$$

where $F_{He}$ is the flow rate of He through in sccm $\min^{-1}$ and $V_C$ is the volume of the catalyst bed. He pressure was kept constant at 30 psig. Each experiment was performed by injecting 1 uL of reactant (cyclic ether or diol) into the reactor followed by immediate separation and quantification of the products.

Reaction products were quantified by separating on a column (Agilent Plot-Q, 30 m, 0.32 mm ID, 20 μm film thickness; temperature program: 40° C. for 2 min, 10° C./min to 270° C., hold 10 min) and detecting with a Polyarc/FID. The Polyarc (Activated Research Company) allows for calibration-free quantitative analysis of hydrocarbons because the FID signal area is proportional to the moles of each compound. Diene selectivity is defined as the ratio of moles of C from the diene divided by the total moles of C from the diene plus the moles of C from all reaction by-products.

$$\text{Diene Selectivity} = \frac{\text{Diene [mol } C]}{\text{Diene [mol } C] + \sum \text{By-products [mol } C]}$$

Diene yield and reactant conversion are defined as follows:

$$\text{Diene Yield} = \frac{\text{Diene [mol } C]}{\sum \text{Reactant and Products [mol } C]}$$

$$\text{Reactant Conversion} = 1 - \frac{\text{Reactant [mol } C]}{\sum \text{Reactant and Products [mol } C]}$$

where Reactant and Products [mol C] refers to all reaction products including the diene and by-products as well as the reactant.

Figure 4:
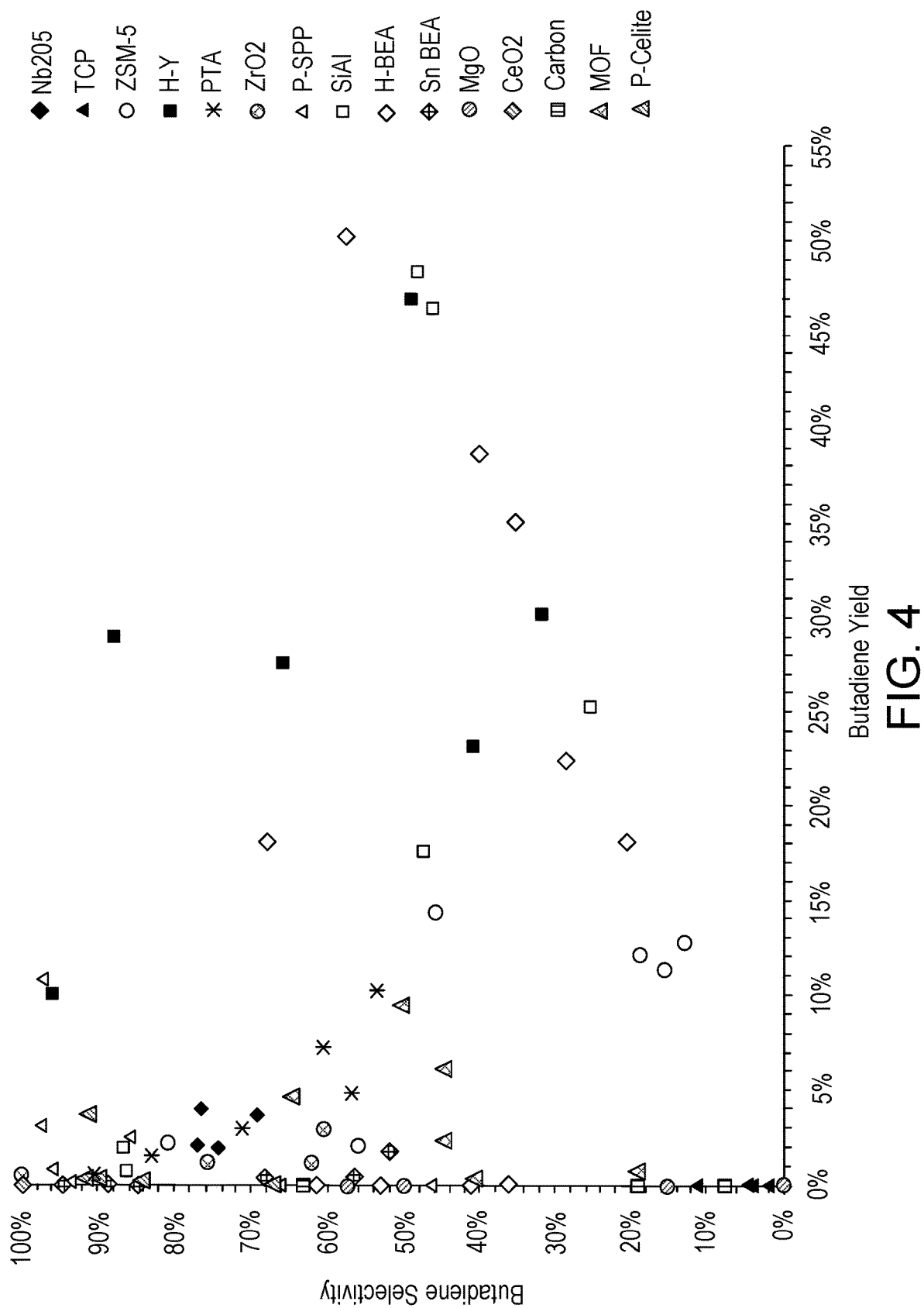
FIG. 4 shows butadiene yield and selectivity formed by the dehydration of tetrahydrofuran (THF) for various catalysts.

FIG. 4 shows a summary of the catalytic data obtained for dehydra-decyclization of THF with various catalysts. Detailed catalytic data for the dehydration of THF to butadiene over fifteen different catalysts are presented in Tables 2-16. Data for 2-methyltetrahydrofuran (2-MTHF) and 2,5-dimethyltetrahydrofuran (2,5-DMTHF) to butadiene are presented in Tables 17 and 18.

TABLE 2

Tetrahydrofuran dehydra-decyclization to butadiene using $CeO_2$
Catalyst $CeO_2$
Mass (mg) 100

| Temperature (° C.) | Space Velocity ($s^{-1}$) | Butadiene Selectivity | Butadiene Yield | THF Conversion |
|---|---|---|---|---|
| 200 | 89 | 1.0000 | 0.0000 | 0.0000 |
| 200 | 10 | 0.5355 | 0.0001 | 0.0001 |
| 300 | 89 | 1.0000 | 0.0000 | 0.0000 |
| 300 | 10 | 0.6157 | 0.0000 | 0.0000 |
| 400 | 89 | 0.3613 | 0.0003 | 0.0008 |
| 400 | 10 | 0.4085 | 0.0004 | 0.0010 |

TABLE 3

Tetrahydrofuran dehydra-decyclization to butadiene using H-ZSM-5 zeolite
Catalyst H-ZSM-5
Mass (mg) 61.8

| Temperature (° C.) | Space Velocity ($s^{-1}$) | Butadiene Selectivity | Butadiene Yield | THF Conversion |
|---|---|---|---|---|
| 200 | 89 | 0.8085 | 0.0209 | 0.0259 |
| 200 | 10 | 0.5603 | 0.0215 | 0.0383 |
| 300 | 89 | 0.4598 | 0.1439 | 0.3109 |
| 300 | 10 | 0.1880 | 0.1203 | 0.6281 |
| 400 | 89 | 0.1546 | 0.1126 | 0.7204 |
| 400 | 10 | 0.1281 | 0.1266 | 0.9875 |

TABLE 4

Tetrahydrofuran dehydra-decyclization to butadiene using H—Y zeolite
Catalyst H—Y
Mass (mg) 45.2

| Temperature (° C.) | Space Velocity ($s^{-1}$) | Butadiene Selectivity | Butadiene Yield | THF Conversion |
|---|---|---|---|---|
| 200 | 89 | 0.9598 | 0.1001 | 0.1043 |
| 200 | 10 | 0.8807 | 0.2903 | 0.3296 |
| 300 | 89 | 0.6589 | 0.2760 | 0.4189 |
| 300 | 10 | 0.4917 | 0.4683 | 0.9524 |
| 400 | 89 | 0.4063 | 0.2310 | 0.5686 |
| 400 | 10 | 0.3162 | 0.3012 | 0.9525 |

TABLE 5

Tetrahydrofuran dehydra-decyclization to butadiene using P-SPP
Catalyst P-SPP
Mass (mg) 42.5

| Temperature (° C.) | Space Velocity ($s^{-1}$) | Butadiene Selectivity | Butadiene Yield | THF Conversion |
|---|---|---|---|---|
| 200 | 89 | 0.4646 | 0.0004 | 0.0008 |
| 200 | 10 | 0.8612 | 0.0016 | 0.0019 |
| 300 | 89 | 0.9379 | 0.0079 | 0.0084 |
| 300 | 10 | 0.9776 | 0.0250 | 0.0256 |
| 400 | 89 | 0.9626 | 0.0308 | 0.0320 |
| 400 | 10 | 0.9731 | 0.1084 | 0.1114 |

TABLE 6

Tetrahydrofuran dehydra-decyclization to butadiene using $ZrO_2$.

Catalyst $ZrO_2$
Mass (mg) 200

| Temperature (° C.) | Space Velocity (s$^{-1}$) | Butadiene Selectivity | Butadiene Yield | THF Conversion |
|---|---|---|---|---|
| 200 | 89 | 0.0000 | 0.0000 | 0.0000 |
| 200 | 10 | 1.0000 | 0.0001 | 0.0001 |
| 300 | 89 | 1.0000 | 0.0056 | 0.0056 |
| 300 | 10 | 0.7570 | 0.0126 | 0.0166 |
| 400 | 89 | 0.6231 | 0.0122 | 0.0196 |
| 400 | 10 | 0.6041 | 0.0288 | 0.0476 |

TABLE 7

Tetrahydrofuran dehydra-decyclization to butadiene using tricalcium phosphate

Catalyst TCP
Mass (mg) 111.7

| Temperature (° C.) | Space Velocity (s$^{-1}$) | Butadiene Selectivity | Butadiene Yield | THF Conversion |
|---|---|---|---|---|
| 200 | 89 | 0.0167 | 0.0000 | 0.0011 |
| 200 | 10 | 0.0204 | 0.0000 | 0.0012 |
| 300 | 89 | 0.0172 | 0.0001 | 0.0040 |
| 300 | 10 | 0.0491 | 0.0003 | 0.0069 |
| 400 | 89 | 0.1139 | 0.0002 | 0.0018 |
| 400 | 10 | 0.0425 | 0.0007 | 0.0105 |

TABLE 8

Tetrahydrofuran dehydra-decyclization to butadiene using $SiO_2$—$Al_2O_3$

Catalyst $SiO_2 \cdot Al_2O_3$
Mass (mg) 200

| Temperature (° C.) | Space Velocity (s$^{-1}$) | Butadiene Selectivity | Butadiene Yield | THF Conversion |
|---|---|---|---|---|
| 200 | 89 | 0.8631 | 0.0076 | 0.0088 |
| 200 | 10 | 0.8688 | 0.0202 | 0.0233 |
| 300 | 89 | 0.4728 | 0.1754 | 0.3710 |
| 300 | 10 | 0.4640 | 0.4640 | 1.0000 |
| 400 | 89 | 0.4833 | 0.4833 | 1.0000 |
| 400 | 10 | 0.2522 | 0.2522 | 1.0000 |

TABLE 9

Tetrahydrofuran dehydra-decyclization to butadiene using H-BEA zeolite

Catalyst H-BEA
Mass (mg) 45.1

| Temperature (° C.) | Space Velocity (s$^{-1}$) | Butadiene Selectivity | Butadiene Yield | THF Conversion |
|---|---|---|---|---|
| 200 | 89 | 0.6813 | 0.1809 | 0.2655 |
| 200 | 10 | 0.5765 | 0.5017 | 0.8702 |
| 300 | 89 | 0.2849 | 0.2234 | 0.7840 |
| 300 | 10 | 0.3982 | 0.3873 | 0.9725 |
| 400 | 89 | 0.2036 | 0.1803 | 0.8857 |
| 400 | 10 | 0.3512 | 0.3512 | 1.0000 |

TABLE 10

Tetrahydrofuran dehydra-decyclization to butadiene using magnesium oxide (MgO)

Catalyst MgO
Mass (mg) 96

| Temperature (° C.) | Space Velocity (s$^{-1}$) | Butadiene Selectivity | Butadiene Yield | THF Conversion |
|---|---|---|---|---|
| 200 | 89 | 0.0000 | 0.0000 | 0.0219 |
| 200 | 10 | 0.0000 | 0.0000 | 0.0001 |
| 300 | 89 | 0.5000 | 0.0000 | 0.0000 |
| 300 | 10 | 0.5733 | 0.0000 | 0.0000 |
| 400 | 89 | 0.0232 | 0.0000 | 0.0010 |
| 400 | 10 | 0.1513 | 0.0002 | 0.0012 |

TABLE 11

Tetrahydrofuran dehydra-decyclization to butadiene using phosphotungstic acid (PTA), $H_3PW_{12}O_{40}$ Catalyst PTA
Mass (mg) 136

| Temperature (° C.) | Space Velocity (s$^{-1}$) | Butadiene Selectivity | Butadiene Yield | THF Conversion |
|---|---|---|---|---|
| 200 | 89 | 0.9042 | 0.0070 | 0.0077 |
| 200 | 10 | 0.8298 | 0.0156 | 0.0188 |
| 300 | 89 | 0.7143 | 0.0308 | 0.0431 |
| 300 | 10 | 0.5704 | 0.0492 | 0.0862 |
| 400 | 89 | 0.6062 | 0.0735 | 0.1213 |
| 400 | 10 | 0.5369 | 0.1018 | 0.1896 |

TABLE 12

Tetrahydrofuran dehydra-decyclization to butadiene using activated carbon (C)

Catalyst C
Mass (mg) 17.7

| Temperature (° C.) | Space Velocity (s$^{-1}$) | Butadiene Selectivity | Butadiene Yield | THF Conversion |
|---|---|---|---|---|
| 200 | 89 | 0.0000 | 0.0000 | 0.0000 |
| 200 | 10 | 0.0000 | 0.0000 | 0.0000 |
| 300 | 89 | 0.0000 | 0.0000 | 0.0001 |
| 300 | 10 | 0.1913 | 0.0000 | 0.0001 |
| 400 | 89 | 0.6331 | 0.0001 | 0.0002 |
| 400 | 10 | 0.0773 | 0.0001 | 0.0012 |

TABLE 13

Tetrahydrofuran dehydra-decyclization to butadiene using metal organic framework (MOF) (MIL 101)

Catalyst MOF
Mass (mg) 25

| Temperature (° C.) | Space Velocity (s$^{-1}$) | Butadiene Selectivity | Butadiene Yield | THF Conversion |
|---|---|---|---|---|
| 150 | 89 | 0.4447 | 0.0615 | 0.1383 |
| 150 | 10 | 0.5049 | 0.0952 | 0.1885 |
| 175 | 89 | 0.4453 | 0.0245 | 0.0549 |
| 175 | 10 | 0.6482 | 0.0485 | 0.0748 |
| 200 | 89 | 0.4041 | 0.0036 | 0.0088 |
| 200 | 10 | 0.1924 | 0.0073 | 0.0379 |

TABLE 14

Tetrahydrofuran dehydra-decyclization to butadiene using niobia ($Nb_2O_5$)

Catalyst $Nb_2O_5$
Mass (mg) 132.5

| Temperature (° C.) | Space Velocity ($s^{-1}$) | Butadiene Selectivity | Butadiene Yield | THF Conversion |
|---|---|---|---|---|
| 200 | 89 | 0.6622 | 0.0002 | 0.0003 |
| 200 | 10 | 0.6217 | 0.0003 | 0.0004 |
| 300 | 89 | 0.7707 | 0.0209 | 0.0271 |
| 300 | 10 | 0.7412 | 0.0197 | 0.0266 |
| 400 | 89 | 0.7636 | 0.0405 | 0.0530 |
| 400 | 10 | 0.6945 | 0.0370 | 0.0533 |

TABLE 15

Tetrahydrofuran dehydra-decyclization to butadiene using Sn-BEA Zeolite

Catalyst Sn-BEA
Mass (mg) 44.1

| Temperature (° C.) | Space Velocity ($s^{-1}$) | Butadiene Selectivity | Butadiene Yield | THF Conversion |
|---|---|---|---|---|
| 200 | 89 | 0.8857 | 0.0001 | 0.0002 |
| 200 | 10 | 0.9443 | 0.0005 | 0.0005 |
| 300 | 89 | 0.8455 | 0.0009 | 0.0011 |
| 300 | 10 | 0.6842 | 0.0046 | 0.0067 |
| 400 | 89 | 0.5676 | 0.0035 | 0.0061 |
| 400 | 10 | 0.5215 | 0.0170 | 0.0327 |

TABLE 16

Tetrahydrofuran dehydra-decyclization to butadiene using P-Celite ®

Catalyst P-Celite ®
Mass (mg) 41.1

| Temperature (° C.) | Space Velocity ($s^{-1}$) | Butadiene Selectivity | Butadiene Yield | THF Conversion |
|---|---|---|---|---|
| 200 | 89 | 0.5015 | 0.0002 | 0.0003 |
| 200 | 10 | 0.6741 | 0.0004 | 0.0006 |
| 300 | 89 | 0.8442 | 0.0018 | 0.0022 |
| 300 | 10 | 0.9023 | 0.0044 | 0.0049 |
| 400 | 89 | 0.9199 | 0.0119 | 0.0130 |
| 400 | 10 | 0.9149 | 0.0372 | 0.0407 |

TABLE 17

2-methyltetrahydrofuran dehydra-decyclization to pentadiene using P-SPP

Catalyst P-SPP
Mass (mg) 42

| Temperature (° C.) | Space Velocity ($s^{-1}$) | Pentadiene Selectivity | Pentadiene Yield | 2-MTHF Conversion |
|---|---|---|---|---|
| 200 | 89 | 0.9788 | 0.0169 | 0.0172 |
| 200 | 10 | 0.9915 | 0.0538 | 0.0542 |
| 300 | 89 | 0.9914 | 0.0822 | 0.0829 |
| 300 | 10 | 0.9726 | 0.2903 | 0.2985 |
| 400 | 89 | 0.9471 | 0.2104 | 0.2221 |
| 400 | 10 | 0.9265 | 0.7009 | 0.7565 |

TABLE 18

2,5-dimethyltetrahydrofuran dehydra-decyclization to hexadiene using P-SPP

Catalyst P-SPP
Mass (mg) 42

| Temperature (° C.) | Space Velocity ($s^{-1}$) | Hexadiene Selectivity | Hexadiene Yield | 2,5 DMTHF Conversion |
|---|---|---|---|---|
| 200 | 89 | 0.9902 | 0.0547 | 0.0553 |
| 200 | 10 | 0.9687 | 0.4061 | 0.4192 |
| 300 | 89 | 0.9830 | 0.2053 | 0.2088 |
| 300 | 10 | 0.9096 | 0.6934 | 0.7624 |
| 400 | 89 | 0.9252 | 0.4075 | 0.4404 |
| 400 | 10 | 0.8101 | 0.8101 | 1.0000 |

Figure 5:
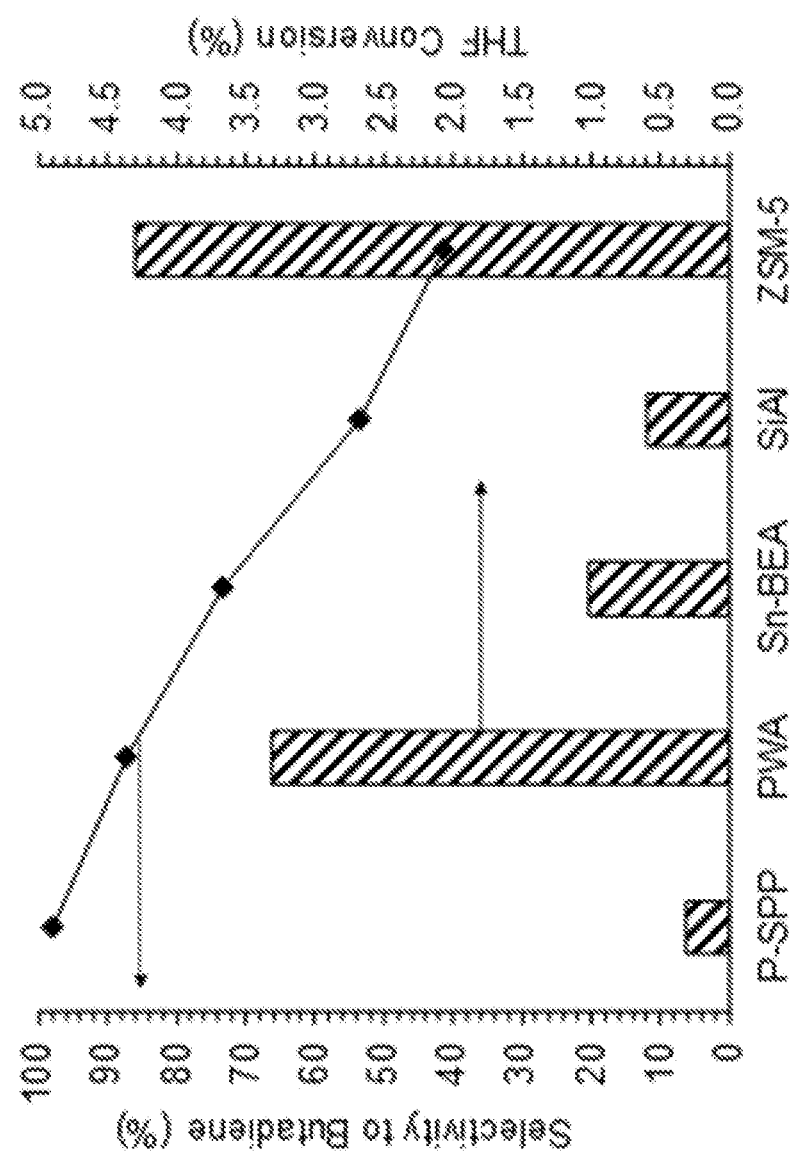
FIG. 5 shows THF conversion and butadiene selectivity for various catalysts.

A variety of solid acid catalysts were tested for the dehydra-decyclization of tetrahydrofuran to butadiene, including: phosphorous acid impregnated self-pillared pentasil (P-SPP), phosphotungstic acid supported on MCM-41 (PWA), tin framework substituted BEA zeolite (Sn-BEA), amorphous silica alumina (SiAl), and Al framework zeolite (ZSM-5). Catalysts were tested in a packed bed flow reactor operated at 250° C. and a weight hourly space velocity of 1 g THF g catalyst$^{-1}$ hf$^{-1}$, with a THF partial pressure of 5 torr. FIG. 5 shows selectivity to butadiene (line plot) and THF conversion (bar graph) for these catalysts. While ZSM-5 provides the highest conversion of THF, it resulted in the lowest selectivity to butadiene. Conversely, P-SPP affords the highest selectivity to butadiene but with the lowest conversion level of THF. PWA provides an optimal intermediate with regards to butadiene yield; the conversion to THF was comparable to ZSM-5 with a relatively high selectivity to butadiene of about 90%.

Preparation and Dehydration of 2-Methyl-1,4-Butanediol

Liquid-phase hydrogenation reactions were performed in 100 mL high pressure reactors (model 4598HPHT, Parr Instrument Co.) equipped with Hastelloy C-276 internals, a magnetic stirrer with gas-entrainment propeller, liquid sampling port, and electronic pressure gauge. 2-methyl-1,4-butanediol was prepared by a previously established method (Spanjers, C. S.; Schneiderman, D. K.; Wang, J. Z.; Wang, J.; Hillmyer, M. A.; Zhang, K.; Dauenhauer, P. J. ChemCatChem 2016, DOI: 10.10). Briefly, 40 g of itaconic acid (Sigma Aldrich) was added to a 100 mL Parr reactor with 20 mL deionized water. To the mixture, 2 g 10 wt. % Pd/C (Sigma Aldrich) was added. The mixture was heated to 220° C. under 140 bar $H_2$ for 3 days. The reactor was subsequently cooled, de-pressurized, and 2.5 g 5 wt. % Ru/C (Sigma Aldrich) was added. The mixture was re-heated to 120° C. under 140 bar $H_2$ for 3 days. The reaction product was filtered and purified in a rotary evaporator to yield 95% pure MBDO.

Dehydration reactions were performed in a high throughput pulsed flow reactor (HTPFR), such as that described with respect to FIG. 3. Experiments were performed at reaction temperatures of 175 to 400° C. The space velocity was controlled by adjusting the carrier gas (He, 99.999%) flow rate to the split vent. Space velocities of 9-400 s' were tested with the reactor, where space velocity is defined previously herein. He pressure was kept constant at 30 psig.

Each experiment was performed by injecting 1 μL of pure MBDO into the reactor followed by immediate separation and quantification of the products. Reaction products were quantified by separating on a column (Agilent Plot-Q, 30 m, 0.32 mm ID, 20 μm film thickness; temperature program:

40° C. for 2 min, 10° C./min to 270° C., hold 10 min) and detecting with a Polyarc/FID. The Polyarc (Activated Research Company) allows for calibration-free quantitative analysis of hydrocarbons because the FID signal area is proportional to the moles of each compound.

Isoprene selectivity is defined previously herein as diene selectivity. The reaction by-products exclude 3-MTHF, because this compound is an intermediate in the production of isoprene and can be recycled. 3-MTHF yield is defined analogously to diene yield.

The following catalysts were tested for 2-methyl-1,4-butanediol dehydration to isoprene: $CeO_2$ (Sigma Aldrich), H-ZSM-5 Zeolite (Zeolyst CBV28014 $SiO_2/Al_2O_3$ ratio=280), H-Y Zeolite (Zeolyst CBV760, $SiO_2/Al_2O_3$=60), H-BEA Zeolite (Zeolyst CBV811C-300 $SiO_2/Al_2O_3$ ratio=360), $ZrO_2$ (Sigma Aldrich), phosphorous-self-pillared pentasil (P-SPP), MgO (Alfa Aesar), tricalcium phosphate (TCP, Sigma Aldrich), $SiO_2.Al_2O_3$(Sigma Aldrich), activated carbon (Sigma Aldrich), metal organic framework catalyst (MOF), niobium oxide ($Nb_2O_5$, Sigma Aldrich), phosphotungstic acid ($H_3PW_{12}O_{40}$, Sigma Aldrich), Sn-BEA Zeolite (Chang C-C, Wang Z, Dornath P, Je Cho H, & Fan W (2012) Rapid synthesis of Sn-Beta for the isomerization of cellulosic sugars. *RSC Advances* 2(28): 10475-10477) and P-Celite (Hong Je Cho, Limin Ren, Vivek Vattipalli, Yu-Hao Yeh, Nicholas Gould, Bingjun Xu, Raymond J. Gorte, Raul Lobo, Paul J. Dauenhauer, Michael Tsapatsis, and Wei Fan, Renewable p-Xylene from 2, 5-Dimethylfuran and Ethylene Using Phosphorus-Containing Zeolite Catalysts *ChemCatChem* 9 (3), 398-402, 2017)). All catalysts were pressed, crushed, and sieved to a particle size of 0.5 to 1 mm. With the exception of MOF MTh 101, all catalysts were pre-treated under flowing He at 400° C. for about 1 hr. MOF MIL 101 was pre-treated under flowing He at 150° C. for 1 hr.

Figure 6:
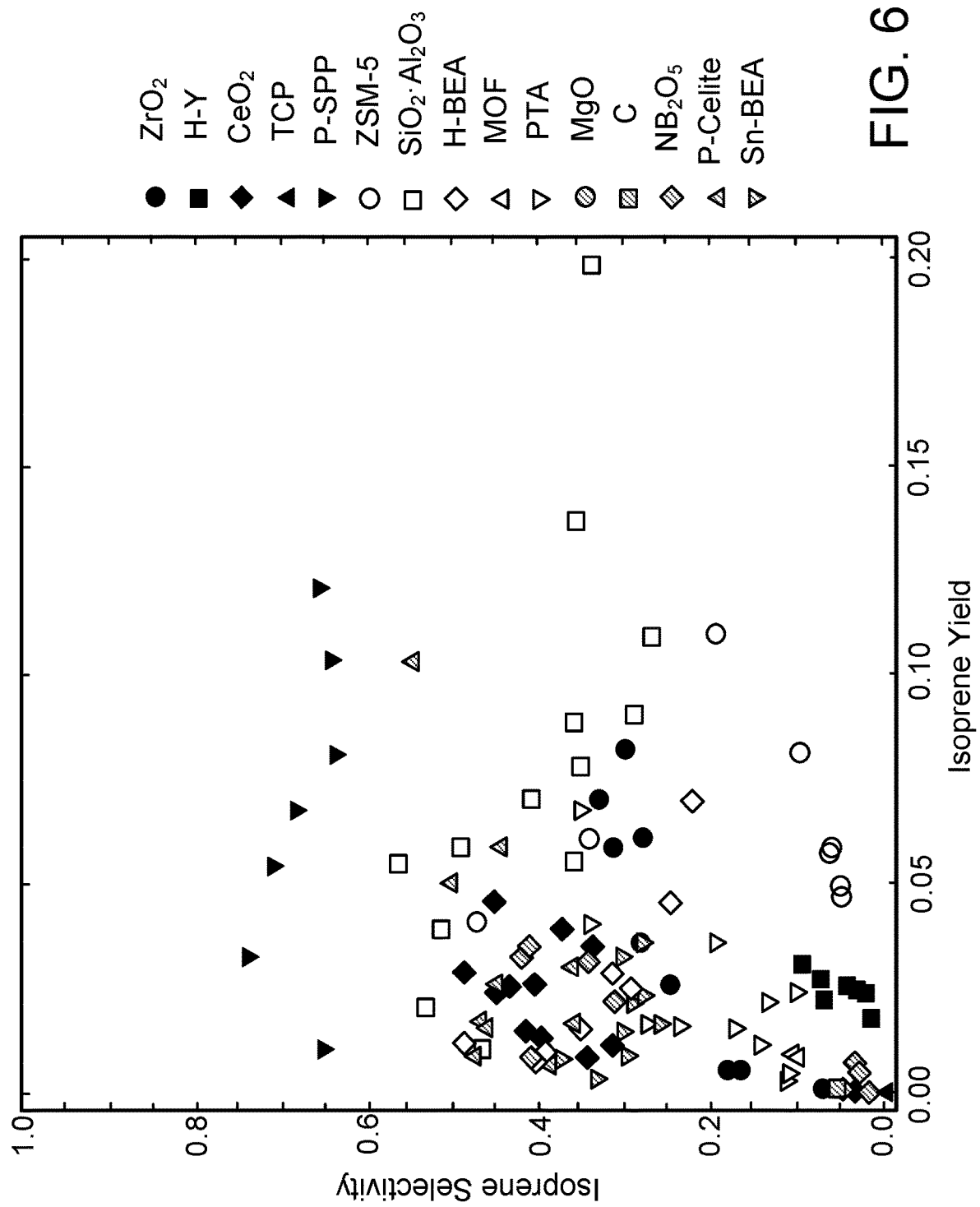
FIG. 6 shows isoprene yield and isoprene selectivity formed by the dehydration of MBDO various catalysts.

FIG. 6 shows a summary of the catalytic data obtained for the illustrative catalysts that were tested. Detailed catalytic data for the dehydration of MBDO to isoprene over fifteen different catalysts are presented in Tables 19-33. Data for the conversion of 3-MTHF to isoprene over P-SPP is presented in Table 34.

TABLE 19

2-methyl-1,4-butanediol dehydration to isoprene using $CeO_2$

Catalyst $CeO_2$
Mass (mg) 100

| Temperature (° C.) | Space Velocity (s$^{-1}$) | Isoprene Selectivity | Isoprene Yield | 3-MTHF Yield | MBDO Conversion |
|---|---|---|---|---|---|
| 200 | 201 | 0.0000 | 0.0000 | 0.0013 | 0.0050 |
| 200 | 101 | 0.0000 | 0.0000 | 0.0010 | 0.0069 |
| 200 | 52 | 0.0000 | 0.0000 | 0.0009 | 0.0055 |
| 200 | 22 | 0.0000 | 0.0000 | 0.0007 | 0.0055 |
| 250 | 201 | 0.0396 | 0.0003 | 0.0113 | 0.0184 |
| 250 | 101 | 0.0353 | 0.0003 | 0.0125 | 0.0209 |
| 250 | 52 | 0.0385 | 0.0003 | 0.0120 | 0.0195 |
| 250 | 22 | 0.0199 | 0.0001 | 0.0090 | 0.0159 |
| 300 | 201 | 0.3480 | 0.0086 | 0.0182 | 0.0428 |
| 300 | 101 | 0.4020 | 0.0132 | 0.0237 | 0.0565 |
| 300 | 52 | 0.4155 | 0.0136 | 0.0231 | 0.0558 |
| 300 | 22 | 0.3179 | 0.0105 | 0.0241 | 0.0572 |
| 350 | 201 | 0.4524 | 0.0241 | 0.0257 | 0.0789 |
| 350 | 101 | 0.4890 | 0.0286 | 0.0382 | 0.0967 |
| 350 | 52 | 0.4410 | 0.0255 | 0.0403 | 0.0982 |

TABLE 19-continued 2-methyl-1,4-butanediol dehydration to isoprene using $CeO_2$

| | | | | | |
|---|---|---|---|---|---|
| 350 | 22 | 0.4129 | 0.0259 | 0.0464 | 0.1092 |
| 400 | 201 | 0.4582 | 0.0453 | 0.0916 | 0.1906 |
| 400 | 101 | 0.3730 | 0.0393 | 0.1279 | 0.2333 |
| 400 | 52 | 0.3376 | 0.0338 | 0.1303 | 0.2305 |
| 400 | 22 | 0.4210 | 0.0308 | 0.1320 | 0.2052 |

TABLE 20

2-methyl-1,4-butanediol dehydration to isoprene using H-ZSM-5 zeolite

| Catalyst | | | H-ZSM-5 Zeolite, $SiO_2/Al_2O_3$ = 280 | | |
|---|---|---|---|---|---|
| Mass (mg) | | | 75 | | |

| Temperature (° C.) | Space Velocity (s$^{-1}$) | Isoprene Selectivity | Isoprene Yield | 3-MTHF Yield | MBDO Conversion |
|---|---|---|---|---|---|
| 200 | 80 | 0.4731 | 0.0407 | 0.9140 | 1.0000 |
| 200 | 9 | 0.3416 | 0.0606 | 0.8225 | 1.0000 |
| 250 | 80 | 0.1937 | 0.1096 | 0.4341 | 1.0000 |
| 250 | 9 | 0.0581 | 0.0581 | 0.0000 | 1.0000 |
| 300 | 80 | 0.0974 | 0.0811 | 0.1671 | 1.0000 |
| 300 | 9 | 0.0466 | 0.0466 | 0.0000 | 1.0000 |
| 350 | 80 | 0.0617 | 0.0576 | 0.0656 | 1.0000 |
| 350 | 9 | 0.0489 | 0.0489 | 0.0000 | 1.0000 |

TABLE 21

2-methyl-1,4-butanediol dehydration to isoprene using H—Y zeolite

| Catalyst | | | H—Y Zeolite, $SiO_2/Al_2O_3$ = 60 | | |
|---|---|---|---|---|---|
| Mass (mg) | | | 65 | | |

| Temperature (° C.) | Space Velocity (s$^{-1}$) | Isoprene Selectivity | Isoprene Yield | 3-MTHF Yield | MBDO Conversion |
|---|---|---|---|---|---|
| 200 | 80 | 0.0941 | 0.0300 | 0.6811 | 1.0000 |
| 200 | 9 | 0.0319 | 0.0232 | 0.2715 | 1.0000 |
| 250 | 80 | 0.0702 | 0.0223 | 0.6825 | 1.0000 |
| 250 | 9 | 0.0384 | 0.0256 | 0.3338 | 1.0000 |
| 300 | 80 | 0.0735 | 0.0273 | 0.6293 | 1.0000 |
| 300 | 9 | 0.0173 | 0.0162 | 0.0591 | 1.0000 |
| 350 | 80 | 0.0404 | 0.0253 | 0.3739 | 1.0000 |
| 350 | 9 | 0.0234 | 0.0234 | 0.0000 | 1.0000 |

TABLE 22

2-methyl-1,4-butanediol dehydration to isoprene using P-SPP

| Catalyst | | | P-SPP | | |
|---|---|---|---|---|---|
| Mass (mg) | | | 7 | | |

| Temperature (° C.) | Space Velocity (s$^{-1}$) | Isoprene Selectivity | Isoprene Yield | 3-MTHF Yield | MBDO Conversion |
|---|---|---|---|---|---|
| 200 | 202 | 0.6516 | 0.0094 | 0.3768 | 0.3913 |
| 250 | 202 | 0.7369 | 0.0321 | 0.4079 | 0.4515 |
| 300 | 202 | 0.7061 | 0.0539 | 0.4821 | 0.5585 |
| 350 | 202 | 0.6798 | 0.0670 | 0.5871 | 0.6857 |
| 400 | 202 | 0.6361 | 0.0804 | 0.6264 | 0.7528 |
| 400 | 103 | 0.6398 | 0.1037 | 0.7374 | 0.8995 |
| 400 | 44 | 0.6560 | 0.1208 | 0.8023 | 0.9865 |

TABLE 23

2-methyl-1,4-butanediol dehydration to isoprene using $ZrO_2$

| Catalyst | $ZrO_2$ |
|---|---|
| Mass (mg) | 200 |

| Temperature (° C.) | Space Velocity ($s^{-1}$) | Isoprene Selectivity | Isoprene Yield | 3-MTHF Yield | MBDO Conversion |
|---|---|---|---|---|---|
| 200 | 89 | 0.0692 | 0.0004 | 0.0683 | 0.0735 |
| 200 | 10 | 0.0659 | 0.0004 | 0.0808 | 0.0867 |
| 250 | 89 | 0.1704 | 0.0052 | 0.1782 | 0.2086 |
| 250 | 10 | 0.1802 | 0.0053 | 0.2501 | 0.2795 |
| 300 | 89 | 0.2828 | 0.0356 | 0.4191 | 0.5451 |
| 300 | 10 | 0.2482 | 0.0261 | 0.6057 | 0.7109 |
| 350 | 89 | 0.3310 | 0.0701 | 0.5992 | 0.8110 |
| 350 | 10 | 0.3186 | 0.0587 | 0.8157 | 1.0000 |
| 400 | 89 | 0.3015 | 0.0816 | 0.7116 | 0.9824 |
| 400 | 10 | 0.2831 | 0.0605 | 0.7864 | 1.0000 |

TABLE 24

2-methyl-1,4-butanediol dehydration to isoprene using tricalcium phosphate

| Catalyst | Tricalcium Phosphate |
|---|---|
| Mass (mg) | 100 |

| Temperature (° C.) | Space Velocity ($s^{-1}$) | Isoprene Selectivity | Isoprene Yield | 3-MTHF Yield | MBDO Conversion |
|---|---|---|---|---|---|
| 200 | 201 | 0.0000 | 0.0000 | 0.0007 | 0.0023 |
| 200 | 101 | 0.0000 | 0.0000 | 0.0004 | 0.0020 |
| 200 | 52 | 0.0000 | 0.0000 | 0.0005 | 0.0020 |
| 200 | 22 | 0.0000 | 0.0000 | 0.0007 | 0.0024 |
| 250 | 201 | 0.0000 | 0.0000 | 0.0004 | 0.0019 |
| 250 | 101 | 0.0000 | 0.0000 | 0.0006 | 0.0021 |
| 250 | 52 | 0.0000 | 0.0000 | 0.0008 | 0.0026 |
| 250 | 22 | 0.0000 | 0.0000 | 0.0011 | 0.0030 |
| 300 | 201 | 0.0000 | 0.0000 | 0.0006 | 0.0017 |
| 300 | 101 | 0.0000 | 0.0000 | 0.0008 | 0.0024 |
| 300 | 52 | 0.0000 | 0.0000 | 0.0011 | 0.0030 |
| 300 | 22 | 0.0000 | 0.0000 | 0.0016 | 0.0035 |
| 350 | 201 | 0.0000 | 0.0000 | 0.0016 | 0.0032 |
| 350 | 101 | 0.0000 | 0.0000 | 0.0025 | 0.0047 |
| 350 | 52 | 0.0000 | 0.0000 | 0.0026 | 0.0046 |
| 350 | 22 | 0.0053 | 0.0000 | 0.0033 | 0.0061 |
| 400 | 201 | 0.0056 | 0.0000 | 0.0113 | 0.0167 |
| 400 | 101 | 0.0079 | 0.0000 | 0.0159 | 0.0200 |
| 400 | 52 | 0.0042 | 0.0000 | 0.0203 | 0.0289 |
| 400 | 22 | 0.0076 | 0.0000 | 0.0261 | 0.0312 |

TABLE 25

2-methyl-1,4-butanediol dehydration to isoprene using $SiO_2 \cdot Al_2O_3$

| Catalyst | $SiO_2 \cdot Al_2O_3$ |
|---|---|
| Mass (mg) | 50 |

| Temperature (° C.) | Space Velocity ($s^{-1}$) | Isoprene Selectivity | Isoprene Yield | 3-MTHF Yield | MBDO Conversion |
|---|---|---|---|---|---|
| 200 | 160 | 0.4698 | 0.0103 | 0.9781 | 1.0000 |
| 225 | 160 | 0.5347 | 0.0202 | 0.9621 | 1.0000 |
| 250 | 160 | 0.5159 | 0.0387 | 0.9251 | 1.0000 |
| 275 | 160 | 0.5687 | 0.0549 | 0.9035 | 1.0000 |
| 300 | 160 | 0.4933 | 0.0586 | 0.8812 | 1.0000 |
| 325 | 160 | 0.4127 | 0.0695 | 0.8316 | 1.0000 |
| 350 | 160 | 0.3554 | 0.0776 | 0.7818 | 1.0000 |
| 375 | 160 | 0.2941 | 0.0905 | 0.6923 | 1.0000 |
| 400 | 160 | 0.2685 | 0.1098 | 0.5910 | 1.0000 |
| 300 | 17 | 0.3413 | 0.1985 | 0.4185 | 1.0000 |
| 300 | 41 | 0.3621 | 0.1366 | 0.6227 | 1.0000 |
| 300 | 81 | 0.3660 | 0.0885 | 0.7582 | 1.0000 |
| 300 | 120 | 0.3641 | 0.0544 | 0.8505 | 1.0000 |

TABLE 26

2-methyl-1,4-butanediol dehydration to isoprene using H-BEA zeolite

| Catalyst | H-BEA Zeolite $SiO_2/Al_2O_3 = 360$ |
|---|---|
| Mass (mg) | 8 |

| Temperature (° C.) | Space Velocity ($s^{-1}$) | Isoprene Selectivity | Isoprene Yield | 3-MTHF Yield | MBDO Conversion |
|---|---|---|---|---|---|
| 200 | 400 | 0.4058 | 0.0072 | 0.2481 | 0.2658 |
| 200 | 44 | 0.4886 | 0.0117 | 0.4937 | 0.5177 |
| 250 | 400 | 0.3963 | 0.0097 | 0.1745 | 0.1990 |
| 300 | 400 | 0.3543 | 0.0149 | 0.2376 | 0.2797 |
| 300 | 44 | 0.3166 | 0.0279 | 0.5778 | 0.6659 |
| 350 | 400 | 0.2968 | 0.0254 | 0.3832 | 0.4686 |
| 400 | 400 | 0.2530 | 0.0449 | 0.6334 | 0.8110 |
| 400 | 44 | 0.2194 | 0.0700 | 0.6571 | 0.9761 |

TABLE 27

2-methyl-1,4-butanediol dehydration to isoprene using magnesium oxide (MgO)

| Catalyst | MgO |
|---|---|
| Mass (mg) | 100 |

| Temperature (° C.) | Space Velocity ($s^{-1}$) | Isoprene Selectivity | Isoprene Yield | 3-MTHF Yield | MBDO Conversion |
|---|---|---|---|---|---|
| 200 | 89 | 0.0000 | 0.0000 | 0.0048 | 0.0048 |
| 200 | 10 | 0.0000 | 0.0000 | 0.0006 | 0.0015 |
| 250 | 89 | 0.0000 | 0.0000 | 0.0032 | 0.0032 |
| 250 | 10 | 0.0000 | 0.0000 | 0.0035 | 0.0053 |
| 300 | 89 | 0.0000 | 0.0000 | 0.0025 | 0.0049 |
| 300 | 10 | 0.0000 | 0.0000 | 0.0052 | 0.0082 |
| 350 | 89 | 0.0000 | 0.0000 | 0.0049 | 0.0106 |
| 350 | 10 | 0.0174 | 0.0002 | 0.0154 | 0.0282 |

TABLE 28

2-methyl-1,4-butanediol dehydration to isoprene using phosphotungstic acid (PTA), $H_3PW_{12}O_{40}$

| Catalyst | PTA |
|---|---|
| Mass (mg) | 100 |

| Temperature (° C.) | Space Velocity ($s^{-1}$) | Isoprene Selectivity | Isoprene Yield | 3-MTHF Yield | MBDO Conversion |
|---|---|---|---|---|---|
| 200 | 89 | 0.1075 | 0.0037 | 0.9658 | 1.0000 |
| 200 | 10 | 0.2715 | 0.0155 | 0.9429 | 1.0000 |
| 250 | 89 | 0.1064 | 0.0050 | 0.9534 | 1.0000 |
| 250 | 10 | 0.1404 | 0.0109 | 0.9226 | 1.0000 |
| 300 | 89 | 0.2344 | 0.0150 | 0.9360 | 1.0000 |
| 300 | 10 | 0.1662 | 0.0152 | 0.8867 | 1.0000 |
| 350 | 89 | 0.3365 | 0.0406 | 0.8793 | 1.0000 |
| 350 | 10 | 0.1305 | 0.0222 | 0.8296 | 1.0000 |
| 400 | 89 | 0.3492 | 0.0682 | 0.8048 | 1.0000 |
| 400 | 10 | 0.1009 | 0.0239 | 0.7632 | 1.0000 |

TABLE 29

2-methyl-1,4-butanediol dehydration to isoprene using activated carbon (C)

| Catalyst Mass (mg) | | | Activated carbon 20 | | |
|---|---|---|---|---|---|
| Temperature (°C.) | Space Velocity ($s^{-1}$) | Isoprene Selectivity | Isoprene Yield | 3-MTHF Yield | MBDO Conversion |
| 200 | 89 | 0.0516 | 0.0005 | 0.0423 | 0.0529 |
| 200 | 10 | 0.0412 | 0.0004 | 0.0151 | 0.0241 |
| 250 | 89 | 0.0486 | 0.0003 | 0.0093 | 0.0156 |
| 250 | 10 | 0.0260 | 0.0002 | 0.0354 | 0.0428 |
| 300 | 89 | 0.0103 | 0.0001 | 0.0167 | 0.0226 |
| 300 | 10 | 0.0195 | 0.0002 | 0.0663 | 0.0743 |
| 350 | 89 | 0.0232 | 0.0002 | 0.0187 | 0.0252 |
| 350 | 10 | 0.0086 | 0.0001 | 0.0827 | 0.0989 |

TABLE 30

2-methyl-1,4-butanediol dehydration to isoprene using metal organic framework (MIL 101)

| Catalyst Mass (mg) | | | MOF 20 | | |
|---|---|---|---|---|---|
| Temperature (°C.) | Space Velocity ($s^{-1}$) | Isoprene Selectivity | Isoprene Yield | 3-MTHF Yield | MBDO Conversion |
| 200 | 89 | 0.0059 | 0.0003 | 0.4034 | 0.4494 |
| 200 | 10 | 0.0028 | 0.0002 | 0.9163 | 0.9925 |
| 250 | 89 | 0.0245 | 0.0014 | 0.8226 | 0.8788 |
| 250 | 10 | 0.0300 | 0.0009 | 0.9679 | 0.9994 |
| 300 | 89 | 0.1059 | 0.0087 | 0.7696 | 0.8515 |
| 300 | 10 | 0.1037 | 0.0077 | 0.9185 | 0.9960 |
| 175 | 89 | 0.0000 | 0.0000 | 0.1142 | 0.1449 |
| 175 | 10 | 0.0000 | 0.0000 | 0.1445 | 0.1720 |
| 150 | 89 | 0.0000 | 0.0000 | 0.0356 | 0.0514 |
| 150 | 10 | 0.0000 | 0.0000 | 0.0366 | 0.0492 |

TABLE 31

2-methyl-1,4-butanediol dehydration to isoprene using niobia ($Nb_2O_5$)

| Catalyst Mass (mg) | | | $Nb_2O_5$ 130 | | |
|---|---|---|---|---|---|
| Temperature (°C.) | Space Velocity ($s^{-1}$) | Isoprene Selectivity | Isoprene Yield | 3-MTHF Yield | MBDO Conversion |
| 200 | 89 | 0.0212 | 0.0002 | 0.1299 | 0.1394 |
| 200 | 10 | 0.0484 | 0.0002 | 0.1501 | 0.1543 |
| 250 | 89 | 0.3807 | 0.0064 | 0.2807 | 0.2974 |
| 250 | 10 | 0.4121 | 0.0082 | 0.3757 | 0.3956 |
| 300 | 89 | 0.4226 | 0.0315 | 0.4830 | 0.5575 |
| 300 | 10 | 0.4145 | 0.0342 | 0.7116 | 0.7940 |
| 350 | 89 | 0.3467 | 0.0313 | 0.7597 | 0.8500 |
| 350 | 10 | 0.3136 | 0.0221 | 0.9295 | 1.0000 |
| 400 | 89 | 0.0317 | 0.0048 | 0.8492 | 1.0000 |
| 400 | 10 | 0.0333 | 0.0066 | 0.8031 | 1.0000 |

TABLE 32

2-methyl-1,4-butanediol dehydration to isoprene using P-Celite ®

| Catalyst Mass (mg) | | | P-Celite ® 35 | | |
|---|---|---|---|---|---|
| Temperature (°C.) | Space Velocity ($s^{-1}$) | Isoprene Selectivity | Isoprene Yield | 3-MTHF Yield | MBDO Conversion |
| 200 | 160 | 0.4818 | 0.0081 | 0.3077 | 0.3246 |
| 200 | 17 | 0.3921 | 0.0065 | 0.2948 | 0.3114 |
| 250 | 160 | 0.4674 | 0.0152 | 0.2661 | 0.2987 |
| 250 | 17 | 0.4710 | 0.0158 | 0.6028 | 0.6362 |
| 300 | 160 | 0.3700 | 0.0165 | 0.4023 | 0.4468 |
| 300 | 17 | 0.4576 | 0.0253 | 0.8165 | 0.8717 |
| 350 | 160 | 0.3690 | 0.0294 | 0.4336 | 0.5133 |
| 350 | 17 | 0.5091 | 0.0502 | 0.8578 | 0.9565 |
| 400 | 160 | 0.4510 | 0.0588 | 0.4713 | 0.6016 |
| 400 | 17 | 0.5542 | 0.1032 | 0.8116 | 0.9978 |

TABLE 33

2-methyl-1,4-butanediol dehydration to isoprene using Sn-BEA zeolite

| Catalyst Mass (mg) | | | Sn-BEA 47.1 | | |
|---|---|---|---|---|---|
| Temperature (°C.) | Space Velocity ($s^{-1}$) | Isoprene Selectivity | Isoprene Yield | 3-MTHF Yield | MBDO Conversion |
| 200 | 89 | 0.3243 | 0.0038 | 0.9884 | 1.0000 |
| 200 | 10 | 0.3322 | 0.0035 | 0.9896 | 1.0000 |
| 250 | 89 | 0.2994 | 0.0087 | 0.9710 | 1.0000 |
| 250 | 10 | 0.3730 | 0.0081 | 0.9784 | 1.0000 |
| 300 | 89 | 0.2613 | 0.0162 | 0.9381 | 1.0000 |
| 300 | 10 | 0.3063 | 0.0137 | 0.9552 | 1.0000 |
| 350 | 89 | 0.2820 | 0.0230 | 0.9183 | 1.0000 |
| 350 | 10 | 0.2924 | 0.0210 | 0.9283 | 1.0000 |
| 400 | 89 | 0.3071 | 0.0315 | 0.8975 | 1.0000 |
| 400 | 10 | 0.2800 | 0.0359 | 0.8717 | 1.0000 |

TABLE 34

3-Methyltetrahydrofuran dehydration to isoprene using P-SPP

| Catalyst Mass (mg) | | | P-SPP 45 | |
|---|---|---|---|---|
| Temperature (°C.) | Space Velocity ($s^{-1}$) | S (Isoprenes) | Y (Isoprenes) | 3-MTHF Conversion |
| 200 | 89 | 0.0796 | 0.0010 | 0.0130 |
| 200 | 10 | 0.5493 | 0.0057 | 0.0103 |
| 250 | 89 | 0.2029 | 0.0044 | 0.0218 |
| 250 | 10 | 0.6294 | 0.0199 | 0.0317 |
| 300 | 89 | 0.3207 | 0.0073 | 0.0229 |
| 300 | 10 | 0.7703 | 0.0493 | 0.0640 |
| 350 | 89 | 0.4036 | 0.0114 | 0.0284 |
| 350 | 10 | 0.7919 | 0.1032 | 0.1303 |
| 400 | 89 | 0.5338 | 0.0211 | 0.0395 |
| 400 | 10 | 0.8230 | 0.1668 | 0.2027 |

Thus, embodiments of methods of forming dienes from cyclic ethers and diols are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A method of forming a diene, the method comprising: contacting a reactant comprising at least one of a cyclic ether and a diol with a heterogeneous acid catalyst to yield a reaction mixture comprising a diene, wherein the heterogeneous acid catalyst comprises a solid acid catalyst, and the solid acid catalyst comprises a phosphorus-containing zeolite catalyst.

2. The method of claim 1, wherein the reactant is derived from biomass.

3. The method of claim 1, wherein the reactant comprises a cyclic ether.

4. The method of claim 3, wherein the cyclic ether has a tetrahydrofuran skeleton.

5. The method of claim 4, wherein the cyclic ether comprises tetrahydrofuran and the diene comprises butadiene.

6. The method of claim 5, wherein a selectivity of the butadiene is at least 95%.

7. The method of claim 3, wherein the cyclic ether comprises 2-methyltetrahydrofuran and the diene comprises pentadiene.

8. The method of claim 7, wherein a selectivity of the pentadiene is at least 95%.

9. The method of claim 3, wherein the cyclic ether comprises 2,5-dimethyltetrahydrofuran and the diene comprises hexadiene.

10. The method of claim 9, wherein a selectivity of the hexadiene is at least 90%.

11. The method of claim 3, the cyclic ether comprises 3-methyltetrahydrofuran and the diene comprises isoprene.

12. The method of claim 11, wherein a selectivity of the isoprene is at least 65%.

13. The method of claim 11, further comprising processing biomass to yield an acid comprising least one of citric acid, itaconic acid, and mesaconic acid, and processing the acid to yield the 3-methyltetrahydrofuran.

14. The method of claim 11, wherein the 3-methyltetrahydrofuran is derived from at least one of citric acid, itaconic acid, and mesaconic acid.

15. The method of claim 1, wherein the reactant comprises a diol.

16. The method of claim 15, wherein the diol comprises 2-methyl-1,4-butanediol, and the diene comprises isoprene.

17. The method of claim 16, wherein a selectivity of the isoprene is at least 70%.

18. The method of claim 1, wherein the contacting occurs at a temperature from 100° C. to 600° C.

19. The method of claim 1, wherein the contacting occurs at a pressure from 0 psia to 500 psia (34 atm).

20. The method of claim 1, wherein the contacting occurs in the presence of an inert gas.

21. The method of claim 20, wherein the inert gas comprises at least one of He, Ar, and $N_2$.

22. The method of claim 1, wherein the contacting occurs in the vapor phase.

23. The method of claim 1, further comprising separating the diene from the reaction mixture.

24. The method of claim 1, wherein the reaction mixture comprises unreacted cyclic ether, unreacted diol, or both, and further comprising contacting the unreacted cyclic ether, unreacted diol, or both with the heterogeneous acid catalyst to yield the diene.

25. The method of claim 1, wherein the phosphorus-containing zeolite catalyst comprises at least one of phosphorus-containing MFI, phosphorus-containing MEL, phosphorus-containing BEA, phosphorus-containing FAU, phosphorus-containing MOR, phosphorus-containing FER, phosphorus-containing CHA, and phosphorus-containing self-pillared pentasil.

26. The method of claim 25, wherein the phosphorus-containing zeolite catalyst comprises phosphorus-containing self-pillared pentasil, and the phosphorus-containing self-pillared pentasil has a ratio of silicon atoms to phosphorus atoms in a range of 1:1 to 1000:1.

27. The method of claim 25, wherein the phosphorus-containing zeolite catalyst comprises phosphorus-containing self-pillared pentasil, and the phosphorus-containing self-pillared pentasil has rotational intergrowths of single-unit-cell lamellae that lead to repetitive branching nanosheets.

28. The method of claim 27, wherein the nanosheets have a thickness of about 2 nm and define a network of micropores having a diameter of about 0.5 nm.

29. The method of claim 25, wherein the phosphorus-containing self-pillared pentasil has a house of cards arrangement defining a network of mesopores having a dimension in a range of 2 nm to 7 nm.

30. The method of claim 1, wherein the phosphorus-containing zeolite catalyst is substantially free of aluminum.

31. The method of claim 30, wherein the phosphorus-containing zeolite catalyst comprises less than 5 wt % of aluminum.

32. The method of claim 18, wherein the contacting occurs at a temperature from 150° C. to 400° C.

33. The method of claim 18, wherein the contacting occurs at a temperature from 100° C. to 500° C.

34. The method of claim 18, wherein the contacting occurs at a temperature from 200° C. to 300° C.

35. The method of claim 1, wherein the contacting occurs at a pressure up to 147 psia (10 atm).

36. The method of claim 18, wherein the contacting occurs at a pressure from 1 atm to 10 atm.

37. The method of claim 36, wherein the contacting occurs at a pressure from 1 atm to 2 atm.

38. The method of claim 26, wherein the phosphorus-containing self-pillared pentasil has a ratio of silicon atoms to phosphorus atoms in a range of 3:1 to 150:1.

39. The method of claim 31, wherein the phosphorus-containing zeolite catalyst comprises less than 4 wt % of aluminum.

40. The method of claim 39, wherein the phosphorus-containing zeolite catalyst comprises less than 3 wt % of aluminum.

41. The method of claim 40, wherein the phosphorus-containing zeolite catalyst comprises less than 2 wt % of aluminum.

42. The method of claim 41, wherein the phosphorus-containing zeolite catalyst comprises less than 1 wt % of aluminum.

* * * * *